(12) United States Patent
Zoellner et al.

(10) Patent No.: US 11,187,699 B2
(45) Date of Patent: Nov. 30, 2021

(54) METHODS AND SYSTEMS FOR PROVIDING LABELLED BIOMOLECULES

(71) Applicant: Becton, Dickinson and Company, Franklin Lakes, NJ (US)

(72) Inventors: Olaf Zoellner, San Diego, CA (US); Eric Jensen, San Diego, CA (US); John Archdeacon, Carlsbad, CA (US); Brent S. Gaylord, San Diego, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 969 days.

(21) Appl. No.: 15/751,143

(22) PCT Filed: Sep. 2, 2016

(86) PCT No.: PCT/US2016/050234
§ 371 (c)(1),
(2) Date: Feb. 7, 2018

(87) PCT Pub. No.: WO2017/041016
PCT Pub. Date: Mar. 9, 2017

(65) Prior Publication Data
US 2018/0231530 A1    Aug. 16, 2018

Related U.S. Application Data

(60) Provisional application No. 62/214,091, filed on Sep. 3, 2015.

(51) Int. Cl.
| | |
|---|---|
| *G01N 33/532* | (2006.01) |
| *G06F 16/248* | (2019.01) |
| *G16C 20/90* | (2019.01) |
| *G06F 7/10* | (2006.01) |
| *G01N 33/58* | (2006.01) |
| *G16B 50/30* | (2019.01) |
| *G06Q 90/00* | (2006.01) |
| *G16C 20/10* | (2019.01) |

(52) U.S. Cl.
CPC ........... *G01N 33/532* (2013.01); *G01N 33/58* (2013.01); *G06F 7/10* (2013.01); *G06F 16/248* (2019.01); *G06Q 90/00* (2013.01); *G16B 50/30* (2019.02); *G16C 20/90* (2019.02); *G16C 20/10* (2019.02)

(58) Field of Classification Search
CPC .... G01N 33/532; G01N 33/58; G06F 16/248; G06F 7/10; G16C 20/90; G06Q 90/00; G16B 50/30
USPC ............................................................ 703/11
See application file for complete search history.

(56) References Cited

U.S. PATENT DOCUMENTS

| | | |
|---|---|---|
| 2003/0120432 A1 | 6/2003 | Zhou et al. |
| 2004/0002818 A1 | 1/2004 | Kulp et al. |
| 2004/0265909 A1 | 12/2004 | Blaney et al. |
| 2006/0100788 A1 | 5/2006 | Carrino et al. |
| 2011/0071048 A1 | 3/2011 | Oshima |
| 2012/0258880 A1 | 10/2012 | Schwartz et al. |
| 2015/0269356 A1 | 9/2015 | Pallai et al. |

FOREIGN PATENT DOCUMENTS

| | | |
|---|---|---|
| JP | 2003331168 | 11/2003 |
| WO | WO2001056216 A2 | 8/2001 |
| WO | WO2001073587 A2 | 10/2001 |
| WO | WO2010006303 A2 | 1/2010 |
| WO | WO2014119624 A1 | 2/2013 |
| WO | WO2013168441 A1 | 11/2013 |
| WO | WO20140047463 A2 | 3/2014 |

*Primary Examiner* — Jerry Lin
(74) *Attorney, Agent, or Firm* — Peter W. Schroen; Bret E. Field; Bozicevic, Field & Francis LLP

(57) ABSTRACT

Aspects of the present disclosure include systems for use in preparing a labelled biomolecule reagent. Systems according to certain embodiments include an input manager for receiving a request for a labelled biomolecule reagent, a memory for storing a dataset having a plurality of labelled biomolecule reagent storage identifiers, a processing module communicatively coupled to the memory and configured to identify one or more labelled biomolecule reagent storage identifiers from the dataset that corresponds to the labelled biomolecule reagent request and an output manager for providing the one or more identified labelled biomolecule reagent storage identifiers. A reagent preparatory apparatus for preparing the labelled biomolecule reagent from an activated biomolecule and activated label is also described. Methods for communicating and receiving a labelled biomolecule reagent request and preparing the subject labelled biomolecule reagents are also provided.

18 Claims, 6 Drawing Sheets

On Demand Conjugates
REQUEST FORM

Format: BV421 — 401A

Clone: CD4 - RPA-T4 — 401B

Quantity (Minimum 50ug): 50 — 402

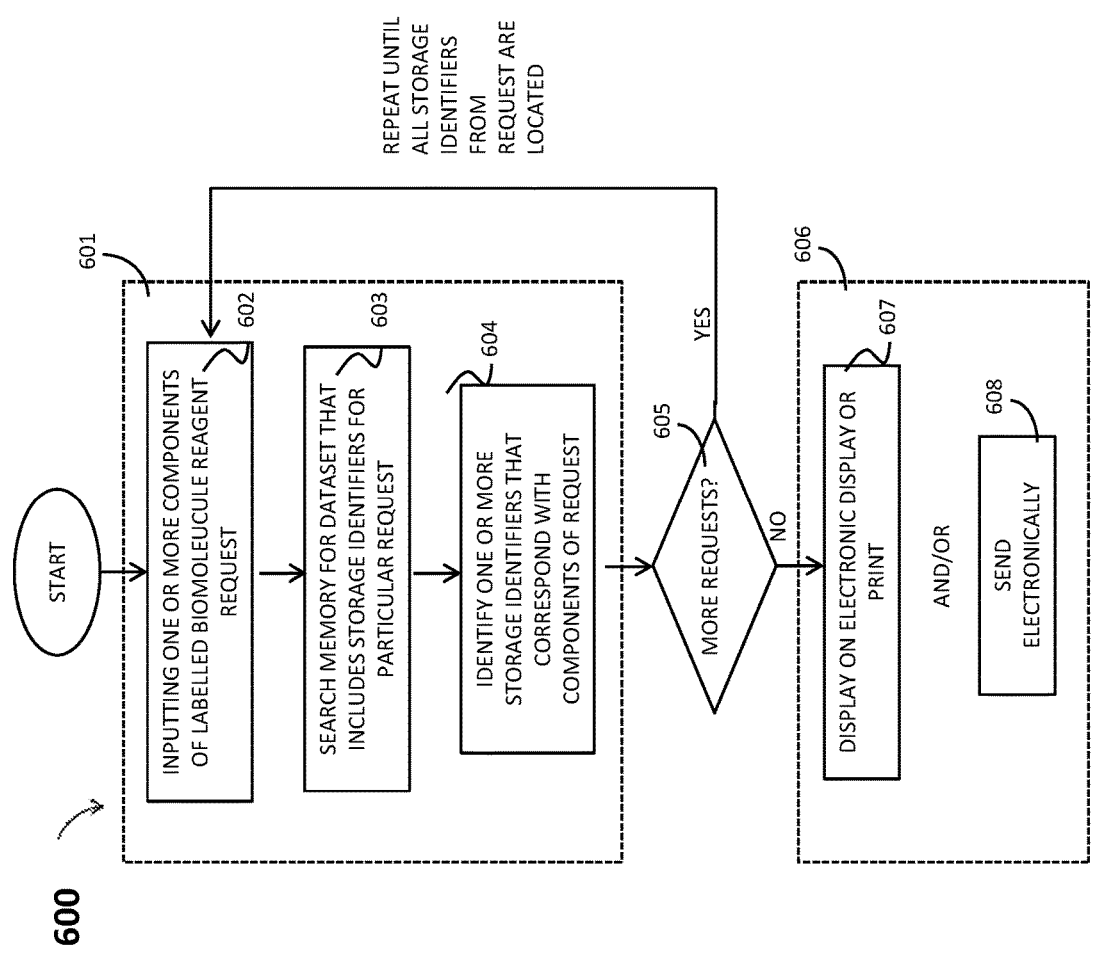

METHODS AND SYSTEMS FOR PROVIDING LABELLED BIOMOLECULES

CROSS-REFERENCE TO RELATED APPLICATIONS

This application claims priority to U.S. Provisional Patent Application Ser. No. 62/214,091 filed Sep. 3, 2015, the disclosure of which application is incorporated herein by reference.

INTRODUCTION

Labelled biomolecule reagent compositions that are used in many analyte assays include a biomolecule that is conjugated to a detectable marker compound. The biomolecule is conjugated to the detectable marker by one or more covalent bonds to the backbone or a side chain of the biomolecule or may be coupled together by ionic or other non-covalent interactions. Often, the biomolecule is a probe compound having a specific binding region for an analyte of interest and the detectable marker is a compound that can visualized, for example under a microscope, with the unaided eye or by some form of optical spectroscopy (e.g., UV-vis, fluorescence spectroscopy, etc.)

Assays for determining the presence and concentration of analytes in a biological fluid often rely on the specific binding of a probe compound. Depending on the analyte of interest, the probe compound may be a polypeptide, such as an antibody or an oligonucleotide, each having a specific binding region. To detect the binding of the target analyte, a marker that can be visualized (e.g., detectable by spectroscopy) is conjugated to the probe compound. Currently, to prepare labelled biomolecule reagents, each biomolecule (e.g., CD4-RPA-T4) is separately conjugated to a detectable label (PE-Cy5) by individual synthetic protocols, followed by purification (e.g., column chromatography). Since each labelled biomolecule reagent is separately prepared and purified, the process of providing an assay-ready specific binding probe composition is expensive and labor intensive, in particular for small scale customer requests. In addition, on-demand preparation of a performance specific and high quality probe composition is not possible due to the amount of lead time necessary for synthesis of the labelled biomolecule and subsequent purification. Commercially, commonly used labelled biomolecule reagents are prepared and stored in advance and customers can only select from a limited database of pre-synthesized labelled biomolecule reagent compositions.

FIG. 1 illustrates the steps for the current commercial preparation of labelled biomolecule reagents used to provide labelled biomolecule reagent compositions for laboratory and clinical assays. A biomolecule (antibody probe) of interest is first purified (step 101) and subjected to reaction conditions (step 102) sufficient to conjugate the biomolecule with five different detectable markers producing labelled biomolecules 100a, 100b, 100c, 100d and 100e. Labelled biomolecules 100a, 100b, 100c, 100d and 100e are then each purified (step 103) and stored. Upon request from a customer, the labelled biomolecules 100a, 100b, 100c, 100d and 100e are formulated into labelled biomolecule reagent compositions and packaged for delivery to the customer.

SUMMARY

Aspects of the invention include a fast, efficient and highly scalable process for delivering high quality and performance specific products across a wide range of biomolecule and detectable label portfolios. In embodiments of the invention, a request for a labelled biomolecule is made and in response to the request the labelled biomolecule is prepared from a pre-existing collection of activated biomolecules and activated labels. FIG. 2 provides an illustration of a method according to an embodiment of the invention. In FIG. 2, a collection of biomolecules (201a) and collection of detectable labels or markers (201b) are first purified. (Step 201) Each biomolecule is then conjugated to a reactive linker to functionalize the biomolecules with a reactive moiety (i.e., activate the biomolecules with reactive linker L1, 202a). The collection of activated biomolecules is then purified and stored. Separately, a collection of detectable markers are also conjugated to reactive linkers to functionalize the collection of detectable markers with a reactive moiety (i.e., activate the labels with reactive linker L2, 202b). The collection of activated labels is also purified and stored (Step 202). Upon request of a labelled biomolecule reagent from a customer, a biomolecule is conjugated to a label by reacting an activated biomolecule (L1) with an activated label (L2) (Step 203) to form labelled biomolecule (bonded through linkage L1-L2). In this way, any desired combination of biomolecule and detectable marker can be prepared on-demand by simply mixing an activated biomolecule with an activated label.

FIG. 3 illustrates this unique and new method of the present disclosure for providing customizable labelled biomolecule reagents on-demand. A biomolecule of interest is purified (step 301) and then functionalized with a reactive linker (step 302) to produce an activated biomolecule 300a. Activated labels 300b, 300c and 300d are separately prepared by functionalizing detectable markers with reactive linkers. Upon receipt of a request from a customer, any combination of activated biomolecule 300a and activated labels 300b, 300c, 300d and 300e can be prepared on-demand by reaction of the reactive linker of activated biomolecule 300a with the reactive linkers of activated labels 300b, 300c, 300d and 300e. Once conjugated, the labelled biomolecules 300a-300b, 300a-300c, 300a-300d and 300a-300e are formulated into labelled biomolecule reagent compositions and packaged for delivery to the customer.

Aspects of the present disclosure also include systems for use in preparing a labelled biomolecule reagent. Systems according to certain embodiments include an input manager for receiving a request for a labelled biomolecule reagent, a memory for storing a dataset having a plurality of labelled biomolecule reagent storage identifiers, a processing module communicatively coupled to the memory and configured to identify one or more labelled biomolecule reagent storage identifiers from the dataset that corresponds to the labelled biomolecule reagent request and an output manager for providing the one or more identified labelled biomolecule reagent storage identifiers. In some embodiments, the request for a labelled biomolecule reagent includes a biomolecule request and a label request. In other embodiments, the request for a labelled biomolecule reagent is a labelled biomolecule request.

The input manager may be operatively coupled to a graphical user interface, such as a website menu interface where the request for a labelled biomolecule reagent is entered into an internet website. In some embodiments, the input manager is configured to receive a labelled biomolecule request. In other embodiments, the input manager is configured to receive a biomolecule request and a label request. The input manager may receive a plurality of labelled biomolecule reagent requests, such as from a single user or from a plurality of users.

The subject systems include memory for storing one or more datasets that include storage identifiers for labelled biomolecules, biomolecules, activated biomolecules, labels, activated labels and reactive linkers. Systems also include a processing module communicatively coupled to the memory that identifies a storage identifier from the one or more datasets that corresponds to the components (e.g., biomolecule request, label request, labelled biomolecule request, etc.) of the labelled biomolecule reagent request. In certain embodiments, an output manager is operatively coupled to a communication component to display the identified storage identifiers, such as on an electronic display or by printing the storage identifiers with a printer.

In certain embodiments, systems of interest further include a reagent preparatory apparatus in operative communication with the output manager for preparing a labelled biomolecule reagent. The reagent preparatory manager is configured to receive the identified storage identifiers from the output manager and produce a labelled biomolecule reagent that corresponds to the labelled biomolecule reagent request.

In embodiments, the reagent preparatory apparatus includes a plurality of activated biomolecules, a plurality of activated labels and sampling device to provide an activated biomolecule and an activated label to a contacting apparatus. In certain instances, the reagent preparatory apparatus includes a reagent analyzer which may be used to characterize, formulate or purify the produced labelled biomolecule reagent, such as by solid phase liquid chromatography.

The biomolecule may be a polypeptide, a nucleic acid or a polysaccharide. In certain embodiments, the biomolecule is a nucleic acid, such as an oligonucleotide, DNA or RNA. In other embodiments, the biomolecule is a polypeptide, such as a protein, an enzyme or an antibody. Labels may include fluorophores, chromophores, enzymes, chemiluminescent substrates, electro-chemiluminescent substrates, redox labels, radio labels, acoustic labels, Raman (SERS) tags, mass tags, isotope tags (e.g., isotopically pure rare earth elements), magnetic particles, microparticles as well as nanoparticles. The labelled biomolecule reagents are prepared by coupling an activated biomolecule with an activated label. The activated biomolecule and activated label each include a reactive linker. In embodiments, the reactive linkers react to form a chemical linkage between the activated biomolecule and the activated linker.

Aspects of the present disclosure also include methods for preparing a labelled biomolecule reagent. Methods according to certain embodiments include receiving a request for a labelled biomolecule reagent, identifying a storage identifier that corresponds with the components of the labelled biomolecule reagent request (e.g., storage identifiers corresponding to a biomolecule request and a label request) and outputting one or more identified storage identifiers. In some embodiments, the identified biomolecule storage identifier and label storage identifier is outputted onto an electronic display or is printed with a printer. In some embodiments, a plurality of requests for labelled biomolecule reagents are received, such as from a single user or a plurality of users. In some instances, the request for the labelled biomolecule reagent may include a plurality of biomolecule requests and a plurality of label requests. In other instances, the request for the labelled biomolecule reagent may include a plurality of biomolecule requests and a single label request. In still other instances, the request for the labelled biomolecule reagent may include a single biomolecule request and a plurality of label requests.

In certain embodiments, methods further include contacting an activated biomolecule with an activated label to produce a labelled biomolecule reagent. In some embodiments, the activated biomolecule and activated label are contacted in a reagent preparatory apparatus. In some instances, the labelled biomolecule reagent is further purified. After preparation, the labelled biomolecule reagent may be packaged and transported to a remote location.

Aspects of the present disclosure also include methods for requesting and receiving a labelled biomolecule reagent. Methods according to certain embodiments include communicating a request for a labelled biomolecule reagent (e.g., to one of the subject systems described herein) and receiving a labelled biomolecule reagent that includes a biomolecule covalently bonded to a label. In some embodiments, communicating a request for a labelled biomolecule reagent includes inputting the biomolecule request and the label request into a graphical user interface, such as a website menu interface on an internet website. In some embodiments, communicating a request for a labelled biomolecule reagent includes inputting a plurality of biomolecule requests and a plurality of label requests. In other embodiments, communicating a request for a labelled biomolecule reagent includes inputting a single biomolecule request and a plurality of label requests. In yet other embodiments, communicating a request for a labelled biomolecule reagent includes inputting a plurality of biomolecule requests and inputting a single label request. In still other embodiments, communicating a request for a labelled biomolecule reagent includes inputting a labelled biomolecule request.

BRIEF DESCRIPTION OF THE FIGURES

FIG. 4 depicts a graphical user interface for communicating a request for a labelled biomolecule reagent according to certain embodiments of the invention.

FIG. 6 illustrates a flow diagram for receiving, processing and outputting a request for a labelled biomolecule reagent according to certain embodiments of the invention.

DETAILED DESCRIPTION

Figure 1:
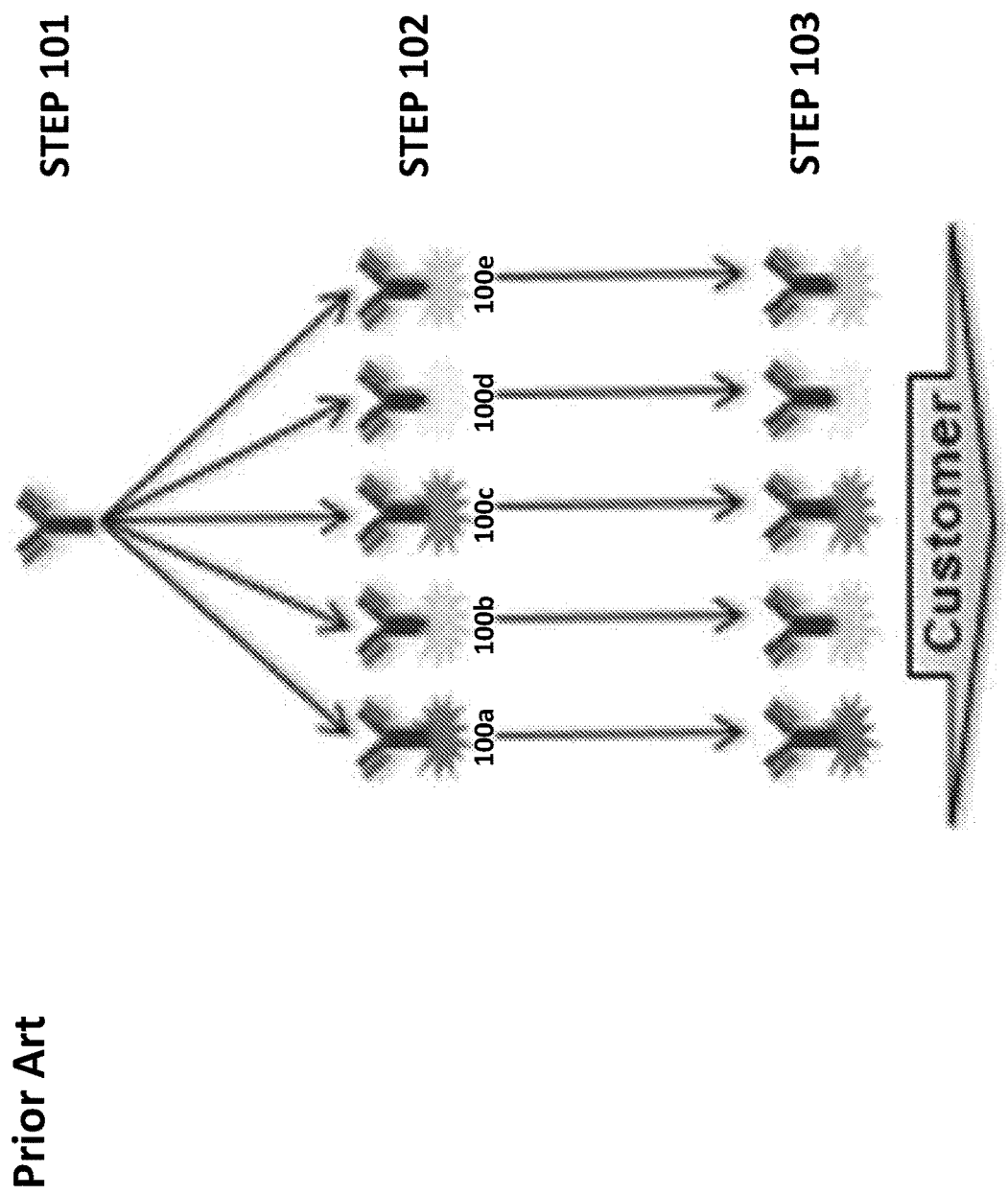
FIG. 1 illustrates the steps for prior art preparation of labelled biomolecule reagents used to provide labelled biomolecule reagent compositions for laboratory and clinical assays.
Figure 2:
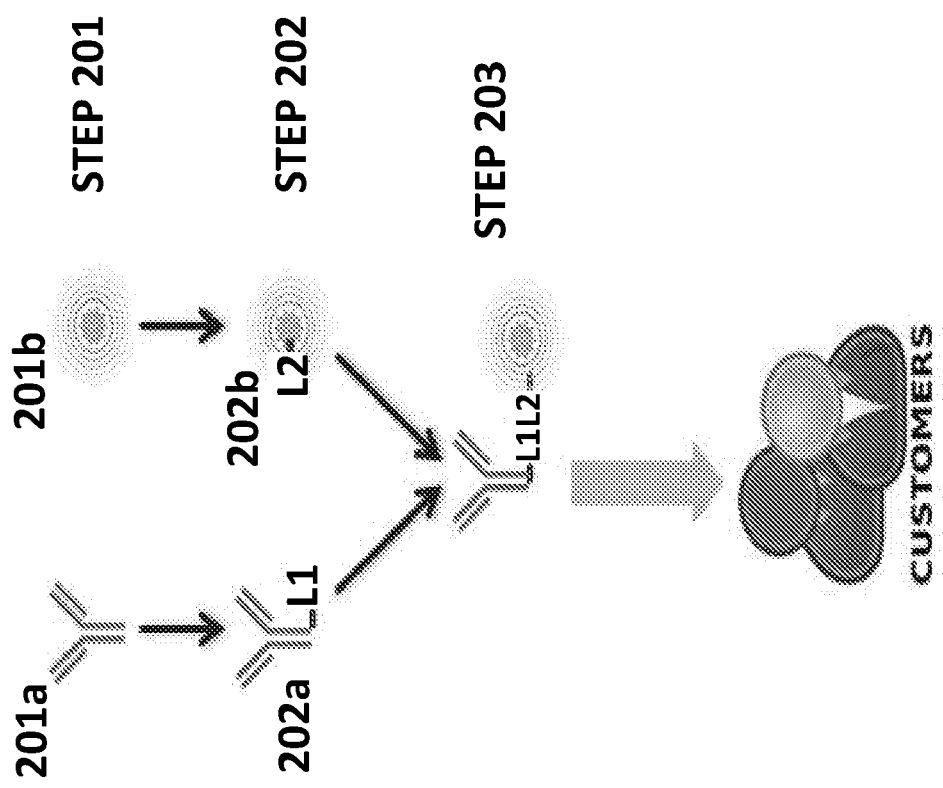
FIG. 2 provides an illustration of a method according to an embodiment of the invention.
Figure 3:
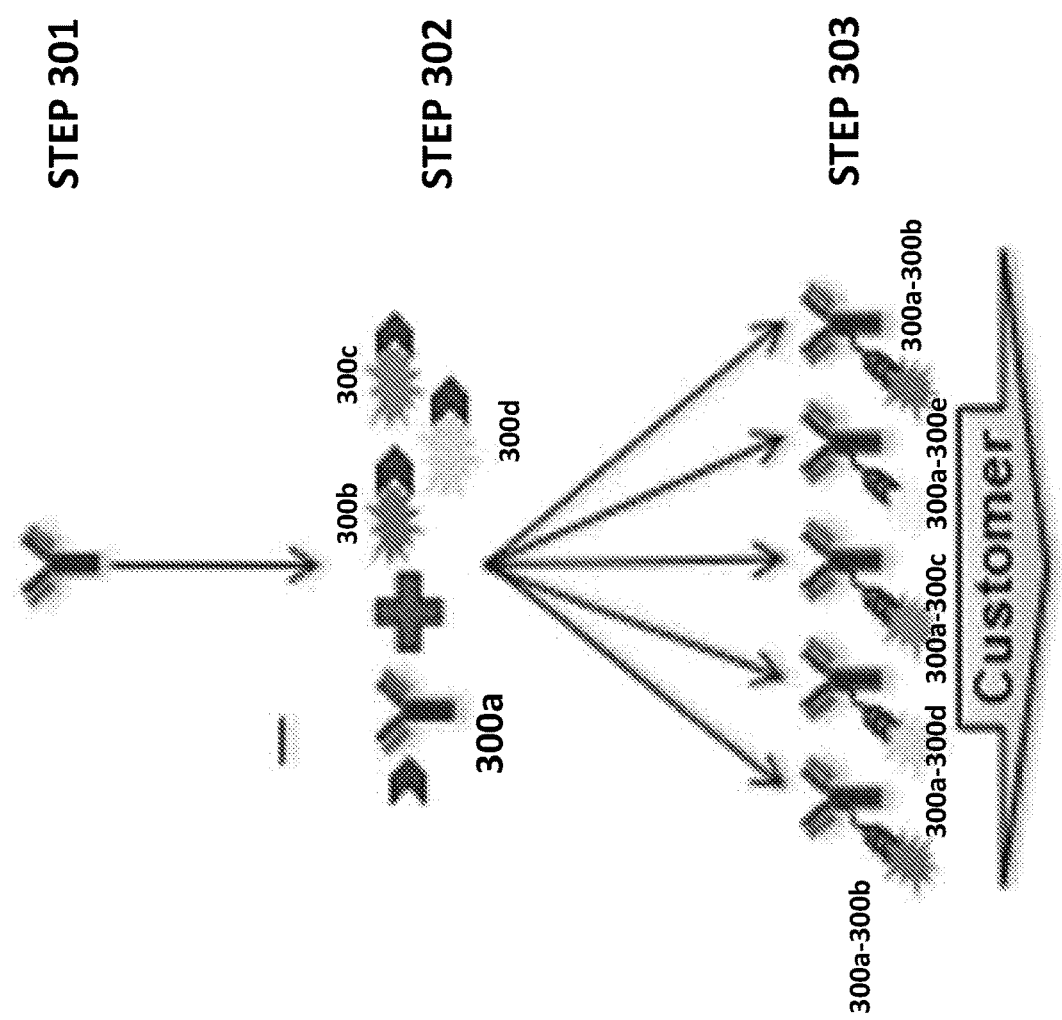
FIG. 3 illustrates a method of the present disclosure for providing customizable labelled biomolecule reagents on-demand.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides systems for use in preparing a labelled biomolecule reagent. In further describing embodiments of the disclosure, systems having an input manager for receiving a labelled biomolecule reagent request and an output manager for providing biomolecule and label storage identifiers are first described in greater detail. Next, a reagent preparatory apparatus for preparing the labelled biomolecule reagent from an activated biomolecule and an activated label are described. Methods for communicating and receiving a labelled biomolecule reagent request and preparing the subject labelled biomolecule reagents are also provided.

Systems for Use in Preparing a Labelled Biomolecule Reagent

Aspects of the present disclosure include systems for use in preparing a labelled biomolecule reagent. Systems according to certain embodiments include an input manager for receiving a request for a labelled biomolecule reagent, a memory for storing a dataset having a plurality of storage identifiers that correspond to the one or more components of the labelled biomolecule reagent request (e.g., biomolecule, label, etc.), a processing module communicatively coupled to the memory and configured to identify a storage identifier from the dataset that corresponds to the components of the labelled biomolecule reagent request and an output manager for providing the identified storage identifiers. As described in greater detail below, the term "labelled biomolecule" reagent refers to a biological macromolecule coupled (e.g., through a covalent bond) to a detectable marker. The biological macromolecule may be a biopolymer. A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. Specifically, a "biopolymer" includes DNA (including cDNA), RNA and oligonucleotides, regardless of the source. As such, biomolecules may include polysaccharides, nucleic acids and polypeptides. For example, the nucleic acid may be an oligonucleotide, truncated or full-length DNA or RNA. In embodiments, oligonucleotides, truncated and full-length DNA or RNA are comprised of 10 nucleotide monomers or more, such as 15 or more, such as 25 or more, such as 50 or more, such as 100 or more, such as 250 or more and including 500 nucleotide monomers or more. For example, oligonucleotides, truncated and full-length DNA or RNA of interest may range in length from 10 nucleotides to $10^8$ nucleotides, such as from $10^2$ nucleotides to $10^7$ nucleotides, including from $10^3$ nucleotides to $10^6$ nucleotides. In embodiments, biopolymers are not single nucleotides or short chain oligonucleotides (e.g., less than 10 nucleotides). By "full length" is meant that the DNA or RNA is a nucleic acid polymer having 70% or more of its complete sequence (such as found in nature), such as 75% or more, such as 80% or more, such as 85% or more, such as 90% or more, such as 95% or more, such as 97% or more, such as 99% or more and including 100% of the full length sequence of the DNA or RNA (such as found in nature)

Polypeptides may be, in certain instances, truncated or full length proteins, enzyme or antibodies. In embodiments, polypeptides, truncated and full-length proteins, enzymes or antibodies are comprised of 10 amino acid monomers or more, such as 15 or more, such as 25 or more, such as 50 or more, such as 100 or more, such as 250 or more and including 500 amino acid monomers or more. For example, polypeptides, truncated and full-length proteins, enzymes or antibodies of interest may range in length from 10 amino acids to $10^8$ amino acids, such as from $10^2$ amino acids to $10^7$ amino acids, including from $10^3$ amino acids to $10^6$ amino acids. In embodiments, biopolymers are not single amino acids or short chain polypeptides (e.g., less than 10 amino acids). By "full length" is meant that the protein, enzyme or antibody is a polypeptide polymer having 70% or more of its complete sequence (such as found in nature), such as 75% or more, such as 80% or more, such as 85% or more, such as 90% or more, such as 95% or more, such as 97% or more, such as 99% or more and including 100% of the full length sequence of the protein, enzyme or antibody (such as found in nature)

In embodiments of the present disclosure, labels are detectable moieties or markers that are detectable based on, for example, fluorescence emission, absorbance, fluorescence polarization, fluorescence lifetime, fluorescence wavelength, absorbance maxima, absorbance wavelength, Stokes shift, light scatter, mass, molecular mass, redox, acoustic, raman, magnetism, radio frequency, enzymatic reactions (including chemiluminescence and electro-chemiluminescence) or combinations thereof. For example, the label may be a fluorophore, chromophore, enzyme, redox label, radiolabels, acoustic label, Raman (SERS) tag, mass tag, isotope tag (e.g., isotopically pure rare earth element), magnetic particle, microparticle as well as a nanoparticle.

Systems include an input manager for receiving a labelled biomolecule reagent request. The labelled biomolecule reagent request may include one or more components. In some instances, the labelled biomolecule reagent request includes a single component and is a labelled biomolecule request (i.e., a request for a biomolecule covalently bonded to a label through a reactive linker). In other instances, the labelled biomolecule reagent request includes two or more components. For example, the labelled biomolecule reagent request includes a biomolecule request and a label request. In certain embodiments, the biomolecule request is an activated biomolecule request that includes a biomolecule and a reactive linker and the label request is an activated label request that includes a label and a reactive linker.

The phrases "labelled biomolecule request", "biomolecule request" and "label request" are used herein to refer to information or data associated with a particular labelled biomolecule, biomolecule or label, respectively. The request may include a string of one or more characters (e.g., alphanumeric characters), symbols, images or other graphical representation(s) associated with a particular labelled biomolecule, biomolecule, label, activated biomolecule, activated label or reactive linker. In some instances, the request is a "shorthand" designation of the labelled biomolecule, biomolecule, label, activated biomolecule, activated label or reactive linker. For example, the request may include an accession number or an abbreviated probe sequence. The request may also include descriptive information, such as chemical structure or reactivity. Information or data, in certain embodiments, may be any suitable identifier of the labelled biomolecule, biomolecule or label and may include, but is not limited to, the name, monomer sequence, sequence identification number, ascension number or biological source of the biomolecule as well as the name, chemical structure, Chemical Abstracts Service (CAS) registry number or marker class (e.g., fluorescence, magnetic) of the label.

In some embodiments, the biomolecule is a biological probe for an analyte of interest and the biomolecule request includes information or data pertaining to a specific binding domain that binds to the analyte of interest. Specific binding domains of interest include, but are not limited to, antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'2 fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

In some instances, the biomolecule is a polypeptide and the biomolecule request may include information such as polypeptide name, protein name, enzyme name, antibody name or the name of protein, enzyme or antibody fragments thereof, polypeptides derived from specific biological fluids (e.g., blood, mucus, lymphatic fluid, synovial fluid, cerebrospinal fluid, saliva, bronchoalveolar lavage, amniotic fluid, amniotic cord blood, urine, vaginal fluid and semen), polypeptides derived from specific species (e.g., mouse monoclonal antibodies) as well as amino acid sequence identification number.

In other instances, the biomolecule is a nucleic acid and the biomolecule request may include information such as oligonucleotide name, oligonucleotides identified by gene name, oligonucleotides identified by accession number, oligonucleotides of genes from specific species (e.g., mouse, human), oligonucleotides of genes associated with specific tissues (e.g., liver, brain, cardiac), oligonucleotides of genes associate with specific physiological functions (e.g., apoptosis, stress response), oligonucleotides of genes associated with specific disease states (e.g., cancer, cardiovascular disease) as well as nucleotide sequence.

As discussed above, labels may include detectable moieties or markers that are detectible based on, for example, fluorescence emission, absorbance, fluorescence polarization, fluorescence lifetime, fluorescence wavelength, absorbance wavelength, Stokes shift, light scatter, mass, molecular mass, redox, acoustic, raman, magnetism, radio frequency, enzymatic reactions (including chemiluminescence and electro-chemiluminescence) or combinations thereof. For example, the label may be a fluorophore, chromophore, enzyme, redox label, radio label, acoustic label, Raman (SERS) tag, mass tag, isotope tag (e.g., isotopically pure rare earth element), magnetic particle, microparticle as well as a nanoparticle. In certain embodiments, the label is a fluorophore (i.e., a fluorescent label, fluorescent dye, etc.). Fluorophores of interest may include but are not limited to dyes suitable for use in analytical applications (e.g., flow cytometry, imaging, etc.), such as an acridine dye, anthraquinone dyes, arylmethane dyes, diarylmethane dyes (e.g., diphenyl methane dyes), chlorophyll containing dyes, triarylmethane dyes (e.g., triphenylmethane dyes), azo dyes, diazonium dyes, nitro dyes, nitroso dyes, phthalocyanine dyes, cyanine dyes, asymmetric cyanine dyes, quinon-imine dyes, azine dyes, eurhodin dyes, safranin dyes, indamins, indophenol dyes, fluorine dyes, oxazine dye, oxazone dyes, thiazine dyes, thiazole dyes, xanthene dyes, fluorene dyes, pyronin dyes, fluorine dyes, rhodamine dyes, phenanthridine dyes, as well as dyes combining two or more of the aforementioned dyes (e.g., in tandem), polymeric dyes having one or more monomeric dye units and mixtures of two or more of the aforementioned dyes thereof. A large number of dyes are commercially available from a variety of sources, such as, for example, Molecular Probes (Eugene, Oreg.), Dyomics GmbH (Jena, Germany), Sigma-Aldrich (St. Louis, Mo.), Sirigen, Inc. (Santa Barbara, Calif.) and Exciton (Dayton, Ohio). For example, the fluorophore may include 4-acetamido-4'-isothiocyanatostilbene-2,2'disulfonic acid; acridine and derivatives such as acridine, acridine orange, acridine yellow, acridine red, and acridine isothiocyanate; allophycocyanin, phycoerythrin, peridinin-chlorophyll protein, 5-(2'-aminoethyl)aminonaphthalene-1-sulfonic acid (EDANS); 4-amino-N-[3-vinylsulfonyl)phenyl] naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcoluarin (Coumaran 151); cyanine and derivatives such as cyanosine, Cy3, Cy3.5, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; dye-conjugated polymers (i.e., polymer-attached dyes) such as fluorescein isothiocyanate-dextran as well as dyes combining two or more dyes (e.g., in tandem), polymeric dyes having one or more monomeric dye units and mixtures of two or more of the aforementioned dyes or combinations thereof.

In some instances, the fluorophore (i.e., dye) is a fluorescent polymeric dye. Fluorescent polymeric dyes that find use in the subject methods and systems are varied. In some instances of the method, the polymeric dye includes a conjugated polymer. Conjugated polymers (CPs) are characterized by a delocalized electronic structure which includes a backbone of alternating unsaturated bonds (e.g., double and/or triple bonds) and saturated (e.g., single bonds) bonds, where π-electrons can move from one bond to the other. As such, the conjugated backbone may impart an extended linear structure on the polymeric dye, with limited bond angles between repeat units of the polymer. For example, proteins and nucleic acids, although also polymeric, in some cases do not form extended-rod structures but rather fold into higher-order three-dimensional shapes. In addition, CPs may form "rigid-rod" polymer backbones and experience a limited twist (e.g., torsion) angle between monomer repeat units along the polymer backbone chain. In some instances, the polymeric dye includes a CP that has a rigid rod structure. As summarized above, the structural characteristics of the polymeric dyes can have an effect on the fluorescence properties of the molecules.

Any convenient polymeric dye may be utilized in the subject methods and systems. In some instances, a polymeric dye is a multichromophore that has a structure capable of harvesting light to amplify the fluorescent output of a fluorophore. In some instances, the polymeric dye is capable of harvesting light and efficiently converting it to emitted light at a longer wavelength. In some cases, the polymeric dye has a light-harvesting multichromophore system that can efficiently transfer energy to nearby luminescent species (e.g., a "signaling chromophore"). Mechanisms for energy transfer include, for example, resonant energy transfer (e.g., Forster (or fluorescence) resonance energy transfer, FRET), quantum charge exchange (Dexter energy transfer) and the like. In some instances, these energy transfer mechanisms are relatively short range; that is, close proximity of the light harvesting multichromophore system to the signaling chromophore provides for efficient energy transfer. Under conditions for efficient energy transfer, amplification of the emission from the signaling chromophore occurs when the number of individual chromophores in the light harvesting multichromophore system is large; that is, the emission from the signaling chromophore is more intense when the incident light (the "excitation light") is at a wavelength which is absorbed by the light harvesting multichromophore system than when the signaling chromophore is directly excited by the pump light.

The multichromophore may be a conjugated polymer. Conjugated polymers (CPs) are characterized by a delocalized electronic structure and can be used as highly responsive optical reporters for chemical and biological targets. Because the effective conjugation length is substantially shorter than the length of the polymer chain, the backbone contains a large number of conjugated segments in close proximity. Thus, conjugated polymers are efficient for light harvesting and enable optical amplification via energy transfer.

In some instances the polymer may be used as a direct fluorescent reporter, for example fluorescent polymers having high extinction coefficients, high brightness, etc. In some instances, the polymer may be used as a strong chromophore where the color or optical density is used as an indicator.

Polymeric dyes of interest include, but are not limited to, those dyes described by Gaylord et al. in US Publication Nos. 20040142344, 20080293164, 20080064042, 20100136702, 20110256549, 20120028828, 20120252986, 20130190193 and 20160025735 the disclosures of which are herein incorporated by reference in their entirety; and Gaylord et al., J. Am. Chem. Soc., 2001, 123 (26), pp 6417-6418; Feng et al., Chem. Soc. Rev., 2010, 39, 2411-2419; and Traina et al., J. Am. Chem. Soc., 2011, 133 (32), pp 12600-12607, the disclosures of which are herein incorporated by reference in their entirety.

In some embodiments, the polymeric dye includes a conjugated polymer including a plurality of first optically active units forming a conjugated system, having a first absorption wavelength (e.g., as described herein) at which the first optically active units absorbs light to form an excited state. The conjugated polymer (CP) may be polycationic, polyanionic and/or a charge-neutral conjugated polymer.

The CPs may be water soluble for use in biological samples. Any convenient substituent groups may be included in the polymeric dyes to provide for increased water-solubility, such as a hydrophilic substituent group, e.g., a hydrophilic polymer, or a charged substituent group, e.g., groups that are positively or negatively charged in an aqueous solution, e.g., under physiological conditions. Any convenient water-soluble groups (WSGs) may be utilized in the subject light harvesting multichromophores. The term "water-soluble group" refers to a functional group that is well solvated in aqueous environments and that imparts improved water solubility to the molecules to which it is attached. In some embodiments, a WSG increases the solubility of the multichromophore in a predominantly aqueous solution (e.g., as described herein), as compared to a multichromophore which lacks the WSG. The water soluble groups may be any convenient hydrophilic group that is well solvated in aqueous environments. In some cases, the hydrophilic water soluble group is charged, e.g., positively or negatively charged or zwitterionic. In certain cases, the hydrophilic water soluble group is a neutral hydrophilic group. In some embodiments, the WSG is a hydrophilic polymer, e.g., a polyethylene glycol, a cellulose, a chitosan, or a derivative thereof.

As used herein, the terms "polyethylene oxide", "PEO", "polyethylene glycol" and "PEG" are used interchangeably and refer to a polymer including a chain described by the formula —($CH_2$—$CH_2$—O—)$_n$- or a derivative thereof. In some embodiments, "n" is 5000 or less, such as 1000 or less, 500 or less, 200 or less, 100 or less, 50 or less, 40 or less, 30 or less, 20 or less, 15 or less, such as 5 to 15, or 10 to 15. It is understood that the PEG polymer may be of any convenient length and may include a variety of terminal groups, including but not limited to, alkyl, aryl, hydroxyl, amino, acyl, acyloxy, and amido terminal groups. Functionalized PEGs that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165. Water soluble groups of interest include, but are not limited to, carboxylate, phosphonate, phosphate, sulfonate, sulfate, sulfinate, ester, polyethylene glycols (PEG) and modified PEGs, hydroxyl, amine, ammonium, guanidinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —$SO_3$M', —$PO_3$M', —$NR_3^+$, Y', ($CH_2CH_2O)_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —($CH_2CH_2O)_{yy}CH_2CH_2XR^{yy}$, —($CH_2CH_2O)_{yy}CH_2CH_2X$—, —X($CH_2CH_2O)_{yy}CH_2CH_2$—, glycol, and polyethylene glycol, wherein yy is selected from 1 to 1000, X is selected from O, S, and $NR^{zz}$, and $R^{zz}$ and $R^{YY}$ are independently selected from H and C1-3 alkyl.

The polymeric dye may have any convenient length. In some cases, the particular number of monomeric repeat units or segments of the polymeric dye may fall within the range of 2 to 500,000, such as 2 to 100,000, 2 to 30,000, 2 to 10,000, 2 to 3,000 or 2 to 1,000 units or segments, or such as 100 to 100,000, 200 to 100,000, or 500 to 50,000 units or segments. In certain instances, the number of monomeric repeat units or segments of the polymeric dye is within the range of 2 to 1000 units or segments, such as from 2 to 750 units or segments, such as from 2 to 500 units or segments, such as from 2 to 250 units or segment, such as from 2 to 150 units or segment, such as from 2 to 100 units or segments, such as from 2 to 75 units or segments, such as from 2 to 50 units or segments and including from 2 to 25 units or segments.

The polymeric dyes may be of any convenient molecular weight (MW). In some cases, the MW of the polymeric dye may be expressed as an average molecular weight. In some instances, the polymeric dye has an average molecular weight of from 500 to 500,000, such as from 1,000 to 100,000, from 2,000 to 100,000, from 10,000 to 100,000 or even an average molecular weight of from 50,000 to 100,000. In certain embodiments, the polymeric dye has an average molecular weight of 70,000.

In certain instances, the polymeric dye includes the following structure:

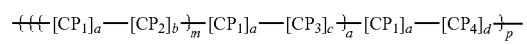

wherein $CP_1$, $CP_2$, $CP_3$ and $CP_4$ are independently a conjugated polymer segment or an oligomeric structure, wherein one or more of $CP_1$, $CP_2$, $CP_3$ and $CP_4$ are bandgap-modifying n-conjugated repeat units.

In some embodiments, the conjugated polymer is a polyfluorene conjugated polymer, a polyphenylene vinylene conjugated polymer, a polyphenylene ether conjugated polymer, a polyphenylene polymer, among other types of conjugated polymers.

In some instances, the polymeric dye includes the following structure:

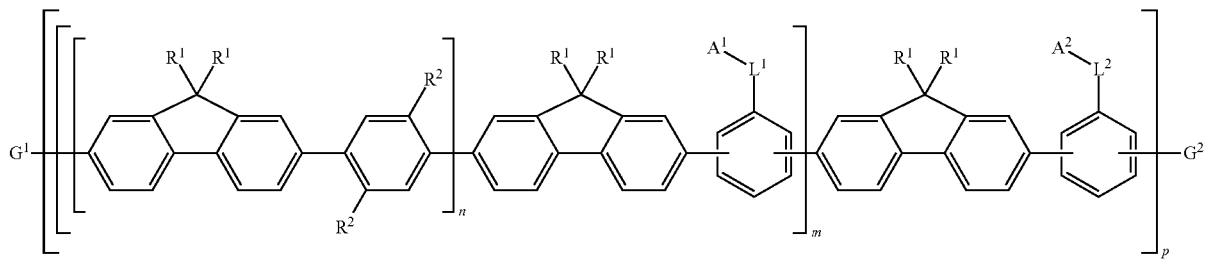

wherein each $R^1$ is independently a solubilizing group or a linker-dye; $L^1$ and $L^2$ are optional linkers; each $R^2$ is independently H or an aryl substituent; each $A^1$ and $A^2$ is independently H, an aryl substituent or a fluorophore; $G^1$ and $G^2$ are each independently selected from the group consisting of a terminal group, a rrconjugated segment, a linker and a linked specific binding member; each n and each m are independently 0 or an integer from 1 to 10,000; and p is an integer from 1 to 100,000. Solubilizing groups of interest include, but is not limited to a water-soluble functional group such as a hydrophilic polymer (e.g., polyalkylene oxide, cellulose, chitosan, etc.), as well as alkyl, aryl and heterocycle groups further substituted with a hydrophilic group such as a polyalkylene oxide (e.g., polyethylglycol including a PEG of 2-20 units), an ammonium, a sulphonium, a phosphonium, as well has a charged (positively, negatively or zwitterionic) hydrophilic water soluble group and the like.

In some cases, the polymeric dye includes, as part of the polymeric backbone, a conjugated segment having one of the following structures:

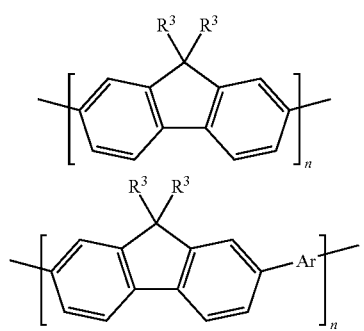

where each $R^3$ is independently an optionally substituted water-soluble functional group such as a hydrophilic polymer (e.g., polyalkylene oxide, cellulose, chitosan, etc.) or an alkyl or aryl group further substituted with a hydrophilic group such as a polyalkylene oxide (e.g., polyethylglycol including a PEG of 2-20 units), an ammonium, a sulphonium, a phosphonium, as well has a charged (positively, negatively or zwitterionic) hydrophilic water soluble group; Ar is an optionally substituted aryl or heteroaryl group; and n is 1 to 10000. In certain embodiments, $R^3$ is an optionally substituted alkyl group. In certain embodiments, $R^3$ is an optionally substituted aryl group. In some cases, $R^3$ is substituted with a polyethyleneglycol, a dye, a chemoselective functional group or a specific binding moiety. In some cases, Ar is substituted with a polyethyleneglycol, a dye, a chemoselective functional group or a specific binding moiety.

In some instances, the polymeric dye includes the following structure:

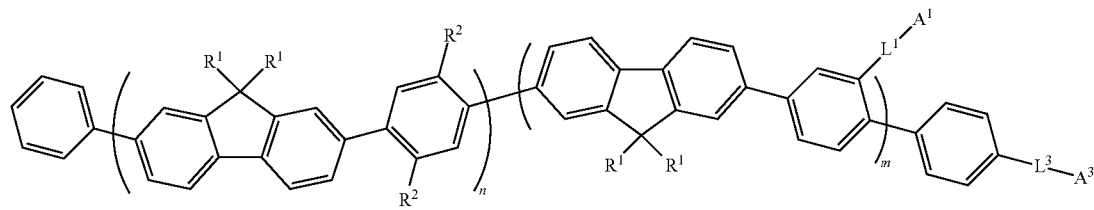

wherein each $R^1$ is a solubilizing group or a linker-dye group; each $R^2$ is independently H or an aryl substituent; $L_1$ and $L_2$ are optional linkers; each $A^1$ and $A^3$ are independently H, a fluorophore, a functional group or a specific binding moiety (e.g., an antibody); and n and m are each independently 0 to 10000, wherein n+m>1.

The polymeric dye may have one or more desirable spectroscopic properties, such as a particular absorption maximum wavelength, a particular emission maximum wavelength, extinction coefficient, quantum yield, and the like (see e.g., Chattopadhyay et al., "Brilliant violet fluorophores: A new class of ultrabright fluorescent compounds for immunofluorescence experiments." Cytometry Part A, 81A (6), 456-466, 2012).

In some embodiments, the polymeric dye has an absorption curve between 280 and 850 nm. In certain embodiments, the polymeric dye has an absorption maximum in the range 280 and 850 nm. In some embodiments, the polymeric dye absorbs incident light having a wavelength in the range between 280 and 850 nm, where specific examples of absorption maxima of interest include, but are not limited to: 348 nm, 355 nm, 405 nm, 407 nm, 445 nm, 488 nm, 640 nm and 652 nm. In some instances, the polymeric dye has an absorption maximum wavelength in a range selected from the group consisting of 280-310 nm, 305-325 nm, 320-350 nm, 340-375 nm, 370-425 nm, 400-450 nm, 440-500 nm, 475-550 nm, 525-625 nm, 625-675 nm and 650-750 nm. In certain embodiments, the polymeric dye has an absorption maximum wavelength of 348 nm. In some instances, the polymeric dye has an absorption maximum wavelength of 355 nm. In some instances, the polymeric dye has an absorption maximum wavelength of 405 nm. In some instances, the polymeric dye has an absorption maximum wavelength of 407 nm. In some instances, the polymeric dye has an absorption maximum wavelength of 445 nm. In some instances, the polymeric dye has an absorption maximum wavelength of 488 nm. In some instances, the polymeric dye has an absorption maximum wavelength of 640 nm. In some instances, the polymeric dye has an absorption maximum wavelength of 652 nm.

In some embodiments, the polymeric dye has an emission maximum wavelength ranging from 400 to 850 nm, such as 415 to 800 nm, where specific examples of emission maxima of interest include, but are not limited to: 395 nm, 421 nm, 445 nm, 448 nm, 452 nm, 478 nm, 480 nm, 485 nm, 491 nm, 496 nm, 500 nm, 510 nm, 515 nm, 519 nm, 520 nm, 563 nm, 570 nm, 578 nm, 602 nm, 612 nm, 650 nm, 661 nm, 667 nm, 668 nm, 678 nm, 695 nm, 702 nm, 711 nm, 719 nm, 737 nm, 785 nm, 786 nm, 805 nm. In some instances, the polymeric dye has an emission maximum wavelength in a range selected from the group consisting of 380-400 nm, 410-430 nm, 470-490 nm, 490-510 nm, 500-520 nm, 560-580 nm, 570-595 nm, 590-610 nm, 610-650 nm, 640-660 nm, 650-700 nm, 700-720 nm, 710-750 nm, 740-780 nm and 775-795 nm. In certain embodiments, the polymeric dye has an emission maximum of 395 nm. In some instances, the polymeric dye has an emission maximum wavelength of 421 nm. In some instances, the polymeric dye has an emission maximum wavelength of 478 nm. In some instances, the polymeric dye has an emission maximum wavelength of 480 nm. In some instances, the polymeric dye has an emission maximum wavelength of 485 nm. In some instances, the polymeric dye has an emission maximum wavelength of 496 nm. In some instances, the polymeric dye has an emission maximum wavelength of 510 nm. In some cases, the polymeric dye has an emission maximum wavelength of 570 nm. In certain embodiments, the polymeric dye has an emission maximum wavelength of 602 nm. In some instances, the polymeric dye has an emission maximum wavelength of 650 nm. In certain cases, the polymeric dye has an emission maximum wavelength of 711 nm. In some instances, the polymeric dye has an emission maximum wavelength of 737 nm. In some instances, the polymeric dye has an emission maximum wavelength of 750 nm. In some embodiments, the polymeric dye has an emission maximum wavelength of 786 nm. In certain instances, the polymeric dye has an emission maximum wavelength of 421 nm±5 nm. In some embodiments, the polymeric dye has an emission maximum wavelength of 510 nm±5 nm. In certain instances, the polymeric dye has an emission maximum wavelength of 570 nm±5 nm. In some instances, the polymeric dye has an emission maximum wavelength of 602 nm±5 nm. In some embodiments, the polymeric dye has an emission maximum wavelength of 650 nm±5 nm. In certain instances, the polymeric dye has an emission maximum wavelength of 711 nm±5 nm. In some cases, the polymeric dye has an emission maximum wavelength of 786 nm±5 nm. In certain embodiments, polymeric dye has an emission maximum selected from the group consisting of 421 nm, 510 nm, 570 nm, 602 nm, 650 nm, 711 nm and 786 nm.

In some instances, the polymeric dye has an extinction coefficient of $1\times10^6$ cm$^{-1}$M$^{-1}$ or more, such as $2\times10^6$ cm$^{-1}$M$^{-1}$ or more, $2.5\times10^6$ cm$^{-1}$M$^{-1}$ or more, $3\times10^6$ cm$^{-1}$M$^{-1}$ or more, $4\times10^6$ cm$^{-1}$M$^{-1}$ or more, $5\times10^6$ cm$^{-1}$M$^{-1}$ or more, $6\times10^6$ cm$^{-1}$M$^{-1}$ or more, $7\times10^6$ cm$^{-1}$M$^{-1}$ or more, or $8\times10^6$ cm$^{-1}$M$^{-1}$ or more. In certain embodiments, the polymeric dye has a quantum yield of 0.05 or more, such as 0.1 or more, 0.15 or more, 0.2 or more, 0.25 or more, 0.3 or more, 0.35 or more, 0.4 or more, 0.45 or more, 0.5 or more, 0.6 or more, 0.7 or more, 0.8 or more, 0.9 or more, 0.95 or more, 0.99 or more and including 0.999 or more. For example, the quantum yield of polymeric dyes of interest may range from 0.05 to 1, such as from 0.1 to 0.95, such as from 0.15 to 0.9, such as from 0.2 to 0.85, such as from 0.25 to 0.75, such as from 0.3 to 0.7 and including a quantum yield of from 0.4 to 0.6. In certain cases, the polymeric dye has a quantum yield of 0.1 or more. In certain cases, the polymeric dye has a quantum yield of 0.3 or more. In certain cases, the polymeric dye has a quantum yield of 0.5 or more. In certain cases, the polymeric dye has a quantum yield of 0.6 or more. In certain cases, the polymeric dye has a quantum yield of 0.7 or more. In certain cases, the polymeric dye has a quantum yield of 0.8 or more. In certain cases, the polymeric dye has a quantum yield of 0.9 or more. In certain cases, the polymeric dye has a quantum yield of 0.95 or more. In some embodiments, the polymeric dye has an extinction coefficient of $1\times10^6$ or more and a quantum yield of 0.3 or more. In some embodiments, the polymeric dye has an extinction coefficient of $2\times10^6$ or more and a quantum yield of 0.5 or more.

The labelled biomolecule reagent is prepared by coupling an activated biomolecule to an activated label. The term "activated" is used herein to refer to a biomolecule or label having a reactive linker or a reactive moiety that, when carried out under appropriate conditions, reacts with a second reactive linker or second reactive moiety to form a chemical linkage, such as for example, an ionic bond (charge-charge interaction), a non-covalent bond (e.g., dipole-dipole or charge-dipole) or a covalent bond. In some embodiments, the reactive linker or moiety of the activated biomolecule reacts with the reactive linker or moiety of the activated label to produce an ionic bond. In other embodiments, the reactive linker or moiety of the activated biomolecule reacts with the reactive linker or moiety of the activated label to produce a non-covalent bond. In yet other embodiments, the reactive linker or moiety of the activated biomolecule reacts with the reactive linker or moiety of the activated label to produce a covalent bond.

In certain embodiments, the reactive linker or moiety of the activated biomolecule reacts with the reactive linker or moiety of the activated label to produce a covalent bond. Any convenient protocol for forming a covalent bond between the reactive linker of the activated biomolecule and the reactive linker of the activated label may be employed, including but not limited to addition reactions, elimination reactions, substitution reactions, pericyclic reactions, photochemical reactions, redox reactions, radical reactions, reactions through a carbene intermediate, metathesis reaction, among other types of bond-forming reactions. In some embodiments, the activated biomolecule may be conjugated to the activated label through reactive linking chemistry such as where reactive linker pairs include, but is not limited to: maleimide/thiol; thiol/thiol;

pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate—periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylate)/thiol and amine/BMPH (N-[3-Maleimidopropionic acid]hydrazide. TFA)/thiol; azide/triarylphosphine; nitrone/cyclooctyne; azide/tetrazine and formylbenzamide/hydrazino-nicotinamide.In certain embodiments, the reactive linker of the activated biomolecule and the reactive linker of the activated label undergo a cycloaddition reaction, such as a [1+2]-cycloaddition, a [2+2]-cycloaddition, a [3+2]-cycloaddition, a [2+4]-cycloaddition, a [4+6]-cycloaddition, or cheleotropic reactions, including linkers that undergo a 1,3-dipolar cycloaddition (e.g., azide-alkyne Huisgen cycloaddition), a Diels-Alder reaction, an inverse electron demand Diels Alder cycloaddition, an ene reaction or a [2+2] photochemical cycloaddition reaction.

In certain embodiments, the biomolecule request and the label request include information or data pertaining to the reactive linker of the activated biomolecule and the activated label. For example, the biomolecule request and the label request may include information or data pertaining to the name of the reactive linker, a chemical structure, a structural description of the reactive linker or the reactive linker CAS number. In certain embodiments, the biomolecule request and the label request includes the name of reactive linker pairs, such as where the reactive linker pairs is may be selected from maleimide/thiol; thiol/thiol; pyridyldithiol/thiol; succinimidyl iodoacetate/thiol; N-succinimidylester (NHS ester), sulfodicholrphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate—periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylate)/thiol and amine/BMPH (N-[β-Maleimidopropionic acid]hydrazide.TFA)/thiol; azide/triarylphosphine; nitrone/cyclooctyne; azide/tetrazine and formylbenzamide/hydrazino-nicotinamide; a diene/a dienophile; and a 1,3-dipole/a dipolarophile.

The input manager is configured to receive the request for the labelled biomolecule. To receive the labelled biomolecule reagent request, the input manager is operatively coupled to a graphical user interface where one or more labelled biomolecule reagents requests are entered. In certain instances, the labelled biomolecule reagent request is entered on an internet website menu interface (e.g., at a remote location) and communicated to the input manager, over the internet or a local area network. In some embodiments, the input manager is configured receive a plurality of labelled biomolecule reagent requests. For example, the input manager may be configured to receive 2 or more labelled biomolecule reagent requests, such as 5 or more, such as 10 or more and including 25 or more labelled biomolecule reagent requests.

Where the request for a labelled biomolecule reagent includes only a single component and is a labelled biomolecule request, the input manager may be configured to receive 2 or more labelled biomolecule requests, such as 5 or more, such as 10 or more and including 25 or more labelled biomolecule requests. Where the labelled biomolecule reagent request includes two components, such as a biomolecule request and a label request, the input manager may be configured to receive 2 or more biomolecule requests, such as 5 or more, such as 10 or more and including 25 or more biomolecule requests and configured to receive 2 or more label requests, such as 5 or more, such as 10 or more and including 25 or more label requests. In some instances, the input manager is configured to receive a labelled biomolecule reagent request that includes a single biomolecule request and single label request. In other instances, the input manager is configured to receive a labelled biomolecule reagent request that includes a single biomolecule request and a plurality of different label requests. In yet other instances, the input manager is configured to receive a labelled biomolecule reagent request that includes a plurality of different biomolecule requests and a single label request. In still other instances, the input manager is configured to receive a labelled biomolecule reagent request that includes a plurality of different biomolecule requests and a plurality of different label requests. The input manager is configured to receive labelled biomolecule requests from a single user or a plurality of different users, such as 2 or more different users, such as 5 or more different users, such as 10 or more different users, such as 25 or more different users and including 100 or more different users.

In embodiments, the input manager is also configured to receive a quantity request corresponding to the desired amount of requested labelled biomolecule reagent. The quantity request may be entered by typing a numerical and a unit (e.g., μg, μmoles, μM, etc.) value into a text box, selecting a check box corresponding to the appropriate numerical and unit values or selecting a numerical value from a first drop-down menu and a unit value from a second drop-down menu.

In some embodiments, the input manager is operatively coupled to one or more searchable databases (e.g., catalog) of labelled biomolecules, activated biomolecules, biomolecules, activated labels, labels and reactive linkers. In certain instances, the input manager includes a database of labelled biomolecules. In other instances, the input manager includes a database of activated biomolecules and activated labels. In yet other instances, the input manager includes a database of biomolecules, labels and reactive linkers.

All or part of each database of labelled biomolecules, activated biomolecules, biomolecules, activated labels, labels and reactive linkers may be displayed on the graphical user interface, such as in a list, drop-down menu or other configuration (e.g., tiles). For example, the graphical user interface may display a list of each labelled biomolecule, activated biomolecule, biomolecule, activated label, label and reactive linkers simultaneously (i.e., on a single screen) or may contain drop-down menus for each component of the labelled biomolecule reagent request. In other embodiments, the labelled biomolecule reagent request is provided by inputting information into appropriate text fields, selecting check boxes, selecting one or more items from a drop-down menu, or by using a combination thereof.

In one example, the graphical user interface includes a drop-down menu to input a labelled biomolecule reagent request by selecting one or more labelled biomolecules from the drop-down menu. In another example, the graphical user interface includes a first drop-down menu to input a biomolecule request and a second drop-down menu to input a label request by selecting one or more biomolecules and one or more labels from the first and second drop-down menus. In yet another example, the graphical user interface includes a first drop-down menu to input a biomolecule request, a second drop-down menu to input a label request and a third drop-down menu to input a reactive linker request by selecting one or more biomolecules, one or more labels and one or more reactive linkers from the drop-down menus. In still another example, the graphical user interface includes a first drop down menu to input an activated biomolecule request and a second drop-down menu to input an activated label request by selecting one or more activated biomolecules and one or more activated linkers from the first and second drop-down menus.

In another example, the graphical user interface includes a list of labelled biomolecules, activated biomolecules, biomolecules, activated labels, labels and reactive linkers that are available in the database. For example, the graphical user interface may display a list of each labelled biomolecule, activated biomolecule, biomolecule, activated label, label and reactive linkers simultaneously on one or more screens or may contain drop-down menus for each component of the labelled biomolecule reagent request. In some instances, a list of all available labelled biomolecules, activated biomolecules, biomolecules, activated labels, labels and reactive linkers displayed on a single page. In other instances, the list of all available labelled biomolecules, activated biomolecules, biomolecules, activated labels, labels and reactive linkers displayed on a plurality of pages, such as 2 or more pages, such as 3 or more pages, such as 5 or more pages, such as 10 or more pages and including 25 or more pages. In yet other instances, the list of all available labelled biomolecules, activated biomolecules, biomolecules, activated labels, labels and reactive linkers are each displayed in separate drop-down menus on a single page.

FIG. 4 depicts a graphical user interface for communicating a request for a labelled biomolecule reagent according to certain embodiments. To communicate the labelled biomolecule reagent request, a user inputs a biomolecule request and a label request onto Request form 400. The label request is inputted by selecting a detectable marker (e.g., a fluorophore) from drop down menu 401A and the biomolecule request is inputted by selecting a biomolecule (e.g., an antibody probe) from drop-down menu 401B. Request form 400 also includes a text box for entering the quantity request 402 corresponding to the desired amount of labelled biomolecule reagent in micrograms.

In certain embodiments, the input manager includes a search engine for searching for, adding or modifying labelled biomolecule reagent requests and for responding to user queries (e.g., inputted into the graphical user interface locally or from a remote location over the internet or local area network). In some instances, each persistent object in the system memory has an associated table in a system database and object attributes are mapped to table columns. In a further aspect, each object has an object relational mapping file which binds that object to the table in the database. Objects are also associated with each other and this association is mapped as the relation between the tables. Objects are also associated with each other by many different relationships, such as one-to-one, one-to-many, many-to-one and many-to-many. Search criteria provided in user queries may include descriptions of attributes or properties associated with an object or by values corresponding to those attributes. Relationships may also be used as search criteria. Basic search criteria can depend upon an object's attributes and advanced search criteria can depend upon association of the object with other objects, e.g., by searching properties of related objects. In certain embodiments, search engines of interest include a finder framework, which will construct a plurality of searchable conditions (e.g., all possible queryable conditions). When a user specifies an entity or object to search for, the framework generates all possible search conditions for that object and then gives the result as per the conditions selected by the user.

Using the search engine, a user of the system can search for available labelled biomolecules, biomolecules, activated biomolecules, labels, activated labels and reactive linkers. The search engine is also configured for searching for pending or completed labelled biomolecule reagent requests. In addition, a user can use the search engine to inquire and find labelled biomolecules, biomolecules, activated biomolecules, labels, activated labels and reactive linkers that may be of interest. For example, a user can search for a particular biomolecule that functions as a specific antigen probe or a label that is detectable by fluorescence of a predetermined wavelength of light. Search conditions may be different for different objects and in one instance, a generic finder framework gives a generic solution for such searching.

In certain embodiments, the search engine can build queries, save queries, modify queries, and/or update queries used to identify labelled biomolecules, biomolecules, activated biomolecules, labels, activated labels or reactive linkers. In some instances, the search results can be shared, compared or modified. In certain instances, systems are configured to set a maximum of search results that fit a search criteria to be displayed on the graphical user interface. In some embodiments, search results are displayed on a Webpage which includes capabilities for allowing possible actions. Such capabilities can include, but are not limited to, links, buttons, drop down menus, fields for receiving information from a user, and the like. In certain aspects, the system further includes a result formatter for formatting search results (e.g., to build appropriate user interfaces such as Web pages, to specify links, provide a way to associate actions (e.g., "delete," "edit," etc.) with images, text, hyperlinks and/or other displays.

The system may also display the search criteria for an object under search on the web page. In one aspect, the system takes input data from the finder framework and creates a web page dynamically showing the search criteria for that object. In another aspect, the finder framework creates all possible queryable conditions for the object under search. These conditions are displayed on search web page as different fields. A user can select or specify value(s) for these field(s) and execute a search. The fields that are to be displayed have their labels in localized form. Fields may be in the form of a "select" box, or a text box or other area for inputting text. For example, a user may desire to search for a biomolecule. Biomolecules in the searchable database include queryable conditions such as compound name or sequence number (e.g., accession number).

In one embodiment, the search engine supports searching for each of the labelled biomolecules, biomolecules, activated biomolecules, labels, activated labels and reactive linkers in the database. In some instances, the system provides a generic finder framework to create all queryable conditions for an object under search. Such conditions will generally depend upon the properties of the object and its relationship(s) with other objects. In other embodiments, the finder framework retrieves localized field names for these conditions and their order and stores these in the system memory (e.g., in an objectdefinition.xml file). In one example, fields are displayed on a search page in the order in which they are stored in a file as a set of search parameters for which a user can select or enter values. The search parameters may be in the form of a list of objects and the parameters may relate to attribute categories. For example, in response to a user searching for a labelled biomolecule, the system may display the queryable conditions: "name of labelled biomolecule," "keywords used for search," "created by," "modified by," "modification date," "annotation" and the like. The finder framework can return the queryable conditions in the form of a collection, which can be displayed on a search page, which lists or represents the various search fields corresponding to the attribute categories in a localized form. A user may enter values for these fields and perform, e.g., selecting one or more of a labelled biomolecule, biomolecule, activated biomolecule, label, activated label and reactive linker having a specific name, structure, registry number, etc., providing specific keywords, identifying a desired domain, creator, modification date, annotation, and the like. The system then displays a list of labelled biomolecules, biomolecules, activated biomolecules, labels, activated labels or reactive linkers that satisfy the search conditions. In certain embodiments, the system displays information regarding the criteria used to perform the search.

In certain embodiments, the input manager includes a labelled biomolecule design platform which is configured to provide a recommendation for choosing one or more biomolecules, activated biomolecules, labels, activated labels or reactive linkers. In some instances, the design platform is configured to provide a recommendation for choosing one or more biomolecules, activated biomolecules, labels, activated labels or reactive linkers based on user input of one or more parameters of the desired labelled biomolecule. For example, parameters of the desired labelled biomolecule which may be inputted by the user into the design platform may include, but are not limited to, desired physical properties of the labelled biomolecule (e.g., molecular mass, melting point, purity, etc.); desired chemical properties of the labelled biomolecule (e.g., chemical structure, structural similarity to a second labelled biomolecule, ionizability, solvation, hydrolysis, chemical reactivity, enzymatic reactivity, binding affinity, etc.); spectroscopic properties (e.g., absorbance wavelength range, absorbance maxima, emission wavelength range, emission maxima, Stokes shift, quantum yield, molar extinction coefficient, etc.) In other instances, the design platform is configured to provide a recomendation for choosing one or more biomolecules, activated biomolecules, labels, activated labels or reactive linkers based on the application of the labelled biomolecule. For example, the design platform may be configured to provide a recommendation for choosing each component of the labelled biomolecule based on instruments that will be used (e.g., flow cytometer, fluorescence spectrometer, etc.), instrument configuration, as well as experimental parameters (e.g., target abundance such as antigen density on a cell). The graphical user interface may include one or more text input fields or drop-down menus for inputting data used by the design platform to provide a recommendation for choosing one or more biomolecules, activated biomolecules, labels, activated labels or reactive linkers.

The labelled biomolecule design platform may be configured to provide a recommendation for a plurality of different biomolecules, activated biomolecules, labels, activated labels or reactive linkers based on information (e.g., properties of the labelled biomolecule or expected application of the labelled biomolecule) inputted by the user. For example, the design platform may be configured to recommend 2 or more different biomolecules, activated biomolecules, labels, activated labels or reactive linkers based on information inputted by the user, such as 3 or more, such as 4 or more, such as 5 or more, such as 10 or more and including 25 or more biomolecules, activated biomolecules, labels, activated labels or reactive linkers.

In certain embodiments, the labelled biomolecule design platform is configured to provide a recommendation as to the combination of biomolecule, label, activated label or reactive linker that is best suited for a particular application (e.g., configuration of a flow cytometer). For example, the design platform may be configured such that a user enters a list of one or more biomolecules and one or more labels as well as application information (e.g., instrument configuration, target abundance, etc.) and the design platform outputs combinations a recommendation of biomolecules, labels, activated labels and reactive linkers best suited for the stated application. In certain embodiments, the recommendation for a labelled biomolecule, biomolecule, activated biomolecule, label, activated label or reactive linker is displayed on a display (e.g., an electronic display) or may be printed with a printer, such as onto a human (paper) readable medium or in a machine readable format (e.g., as a barcode). In other embodiments, the recommendation for a labelled biomolecule, biomolecule, activated biomolecule, label, activated label or reactive linker may be communicated to the input manager and the recommended labelled biomolecule may be prepared as described above.

Systems of the present disclosure also include a memory for storing a dataset having a plurality of storage identifiers that correspond with the components the of the label biomolecule reagent request. The term "memory" is used herein in its conventional sense to refer to a device that stores information for subsequent retrieval by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices). The memory may be a computer readable medium or permanent memory. In embodiments, the memory may include one or more datasets having a plurality of storage identifiers that correspond to each labelled biomolecule, biomolecule, label, activated biomolecule, activated label and reactive linker in the system database.

The datasets stored in the memory include storage identifiers that correspond with each labelled biomolecule, biomolecule, label, activated biomolecule, activated label or reactive linker. The storage identifiers may be presented in the dataset as a string of one or more characters (e.g., alphanumeric characters), symbols, images or other graphical representation(s) associated with a particular labelled biomolecule, biomolecule, label, activated biomolecule, activated label or linker. In some instances, the storage identifier is abbreviated designation of the labelled biomolecule, biomolecule, label, activated biomolecule, activated label or linker. For example, the storage identifier may include references to accession number, sequence identification number, identifiable probe sequence, CAS registry number or may be a custom identification code.

The number of storage identifiers in each dataset stored in memory may vary, depending on the type of storage identifiers. For example, the dataset stored in memory having a plurality of labelled biomolecule storage identifiers may include 10 or more labelled biomolecule storage identifiers, such as 25 or more, such as 50 or more, such as 100 or more identifiers, such 250 or more, such as 500 or more and including 1000 or more labelled biomolecule storage identifiers. The dataset stored in memory having a plurality of biomolecules or activated biomolecules may include 25 or more biomolecule or activated biomolecule storage identifiers, such as 50 or more, such as 100 or more, such as 250 or more, such as 500 or more and including 1000 or more biomolecule or activated biomolecule storage identifiers. The dataset stored in memory having a plurality of labels or activated labels may include 5 or more label or activated label storage identifiers, such as 10 or more, such as 15 or more, such as 25 or more and including 50 or more label or activated label storage identifiers. In certain embodiments, the dataset stored in memory having a plurality of reactive linkers includes 2 or more reactive linker storage identifiers, such as 3 or more, such as 5 or more, such as 10 or more and including 15 or more reactive linker storage identifiers.

The memory is in operative communication with a processing module that identifies one or more storage identifiers from the dataset that corresponds to the request received by the input manager. In some embodiments, the request for a labelled biomolecule reagent is a labelled biomolecule request and the processing module identifies a labelled biomolecule storage identifier from a dataset in the memory having a plurality of labelled biomolecules storage identifiers. In other embodiments, the request for a labelled biomolecule reagent includes a biomolecule request and a label request and the processing module identifies: 1) a biomolecule storage identifier from a first dataset in the memory having a plurality of biomolecule storage identifiers; and 2) a label storage identifier from a second dataset in the memory having a plurality of label storage identifiers. In still other embodiments, the request for a labelled biomolecule reagent includes a biomolecule request, a label request and a reactive linker request and the processing module identifies: 1) a biomolecule storage identifier from a first dataset in the memory having a plurality of biomolecule storage identifiers; 2) a label storage identifier from a second dataset in the memory having a plurality of label storage identifiers; and 3) a reactive linker storage identifier from a third dataset in the memory having a plurality of reactive linker storage identifiers.

When a particular storage identifier that corresponds to a labelled biomolecule request, biomolecule request, label request, activated biomolecule request, activated label request or reactive linker request are not available (i.e., cannot be identified by the processing module from any dataset in the memory), the memory may include algorithm for providing a recommendation for an alternative labelled biomolecule, biomolecule, label, activated biomolecule, activated label or reactive linker. The recommendation may be based on similarities in chemical structure, reactivity, probe target, binding affinity, target abundance, target density, label cross-talk, size, price, etc. as the requested labelled biomolecule, biomolecule, label, activated biomolecule, activated label or reactive linker. The memory may be configured to provide a recommendation for one or more alternatives, such as 2 or more alternatives, such as 3 or more alternatives and including 5 or more alternatives, depending on the similarity between the requested component and available labelled biomolecule, biomolecule, label, activated biomolecule, activated label or reactive linkers.

The processing module may include a commercially available processor such as a processor made by Intel Corporation, a SPARC® processor made by Sun Microsystems, or it may be one of other processors that are or will become available. The processor executes the operating system, which may be, for example, a WINDOWS®-type operating system from the Microsoft Corporation; a Unix® or Linux-type operating system or a future operating system; or some combination thereof. The operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

Processing modules of the subject systems include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include WINDOWS NT®, Sun Solaris, Linux, OS/400, Compaq Tru64 Unix, SGI IRIX, Siemens Reliant Unix, and others. Other development products, such as the Java™2 platform from Sun Microsystems, Inc. may be employed in processors of the subject systems to provide suites of applications programming interfaces (API's) that, among other things, enhance the implementation of scalable and secure components. Various other software development approaches or architectures may be used to implement the functional elements of system and their interconnection, as will be appreciated by those of ordinary skill in the art.

Systems of the present disclosure also include an output manager that provides the identified storage identifiers from the processing module. In some embodiments, the output manager includes an electronic display and the identified storage identifiers are outputted onto the electronic display. One or more storage identifiers may be outputted onto the electronic display simultaneously, such as 2 or more, such as 3 or more, such as 5 or more, such as 10 or more, such as 25 or more, such as 100 or more and including 500 or more storage identifiers. The output manager may display the storage identifiers of the labelled biomolecule reagent requests from a single user or from a plurality of users, such as from 2 or more users, such as 5 or more users, such as 10 or more users, such as 25 or more users and including 100 or more users. The output manager may be configured to organize the displayed storage identifiers, as desired, such as grouping the storage identifiers according to each request for a labelled biomolecule, by user or by type of storage identifier (e.g., labelled biomolecule storage identifier, biomolecule storage identifier, label storage identifier, reactive linker storage identifier). In other embodiments, the output manager includes a printer and the identified storage identifiers are printed onto a human (paper) readable medium or as in a machine readable format (e.g., as a barcode).

In certain embodiments, the output manager communicates the storage identifiers assembled by the processing module, e.g., one or more labelled biomolecule storage identifiers, biomolecule storage identifiers, label storage identifiers, reactive linker storage identifiers in an electronic format to a user, such as over a local area network or over the Internet. The electronic communication of data by the output manager may be implemented according to a convenient protocol, including but not limited to, SQL, HTML or XML documents, email or other files, or data in other forms. The data may also include Internet URL addresses so that a user may retrieve additional SQL, HTML, XML, or other documents or data from remote sources.

Systems of the present disclosure for inputting a labelled biomolecule reagent request, storing a plurality of storage identifiers that correspond with the components the of the label biomolecule reagent request, identifying one or more storage identifiers and for outputting the identified storage identifiers include a computer. In certain embodiments, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer that runs the program and returns an output to the user.

A system can, in certain embodiments, include a computer that includes: a) a central processing unit; b) a main non-volatile storage drive, which can include one or more hard drives, for storing software and data, where the storage drive is controlled by disk controller; c) a system memory, e.g., high speed random-access memory (RAM), for storing system control programs, data, and application programs, including programs and data loaded from non-volatile storage drive; system memory can also include read-only memory (ROM); d) a user interface, including one or more input or output devices, such as a mouse, a keypad, and a display; e) an optional network interface card for connecting to any wired or wireless communication network, e.g., a printer; and f) an internal bus for interconnecting the aforementioned elements of the system.

The memory of a computer system can be any device that can store information for retrieval by a processor, and can include magnetic or optical devices, or solid state memory devices (such as volatile or non-volatile RAM). A memory or memory unit can have more than one physical memory device of the same or different types (for example, a memory can have multiple memory devices such as multiple drives, cards, or multiple solid state memory devices or some combination of the same). With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, floppy disk and DVD are all examples of permanent memory. Random Access Memory (RAM) is an example of non-permanent (i.e., volatile) memory. A file in permanent memory can be editable and re-writable.

Operation of the computer is controlled primarily by an operating system, which is executed by the central processing unit. The operating system can be stored in a system memory. In some embodiments, the operating system includes a file system. In addition to an operating system, one possible implementation of the system memory includes a variety of programming files and data files for implementing the method described below. In certain cases, the programming can contain a program, where the program can be composed of various modules, and a user interface module that permits a user to manually select or change the inputs to or the parameters used by the program. The data files can include various inputs for the program.

In certain embodiments, instructions in accordance with the method described herein can be coded onto a computer-readable medium in the form of "programming," where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programs that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

In any embodiment, data can be forwarded to a "remote location," where "remote location," means a location other than the location at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

Some embodiments include implementation on a single computer, or across a network of computers, or across networks of networks of computers, for example, across a network cloud, across a local area network, on hand-held computer devices, etc. In certain embodiments, one or more of the steps described herein are implemented on a computer program(s). Such computer programs execute one or more of the steps described herein. In some embodiments, implementations of the subject method include various data structures, categories, and modifiers described herein, encoded on computer-readable medium(s) and transmissible over communications network(s).

Software, web, internet, cloud, or other storage and computer network implementations of the present invention could be accomplished with standard programming techniques to conduct the various assigning, calculating, identifying, scoring, accessing, generating or discarding steps.

Figure 5:
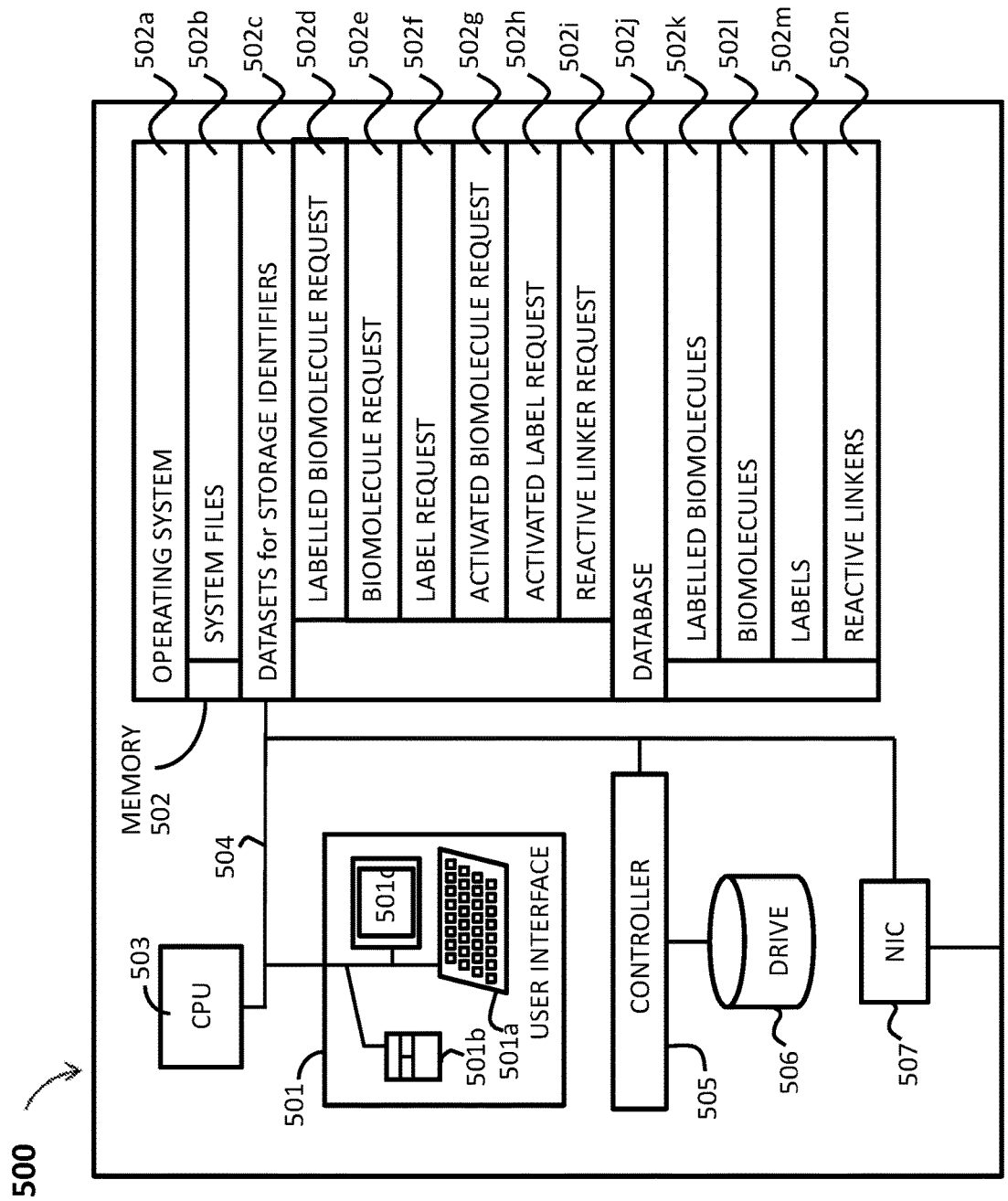
FIG. 5 depicts a computer system of the present disclosure according to certain embodiments of the invention.

FIG. 5 depicts a computer system 500 of the present disclosure according to certain embodiments. The computer system includes user interface 501 that includes a keyboard 501a, a mouse 501b and monitor 501c for inputting a labelled biomolecule reagent request. User interface 501 is operatively coupled to a memory 502 that includes operating system 502a, system files 502b and datasets that include a plurality of storage identifiers that correspond to the components of the labelled biomolecule reagent request: 1) labelled biomolecule request 502d; 2) biomolecule request 502e; 3) label request 502f; 4) activated biomolecule request 502g; 5) activated label request 502h; and 6) reactive linker request 502i. Memory 502 also includes a database 502j that includes a searchable inventory listing of labelled biomolecules 502k, biomolecules 502l, labels 502m and reactive linkers 502n.

The memory and user interface are operatively coupled to a processor 503 through connection 504 that includes a storage drive 506 that is controlled by disk controller 505. As described above, the processor identifies one or more storage identifiers from the dataset that corresponds to the request received by the input manager.

To output the identified storage identifiers, systems of interest according to this embodiment include a network interface controller 507 which outputs the storage identifiers. Network interface controller 507 may be interfaced with an electronic display to visually display the identified storage identifiers or may be interfaced with a printer for presenting the identified storage identifiers onto a human (paper) readable medium or as in a machine readable format (e.g., as a barcode). In certain instances, network interface controller 507 communicates the storage identifiers in an electronic format, such as over a local area network or over the internet and may be implemented according to any electronic format, including but not limited to, SQL, HTML or XML documents, email or other files, or data in other forms.

FIG. 6 illustrates a flow diagram 600 for receiving, processing and outputting a request for a labelled biomolecule reagent according to certain embodiments. Receiving and processing 601 the request starts with inputting the one or more components of the labelled biomolecule reagent request (602). As discussed above, the labelled biomolecule reagent request may include one or more of 1) a labelled biomolecule request; and 2) a biomolecule request and a label request. In some instances, the biomolecule request is an activated biomolecule request where biomolecule is coupled to a reactive linker. In other instances, the label request is an activated label request where the label is coupled to a reactive linker.

After the systems has received the labelled biomolecule reagent request, a processor determines the components of the request (i.e., labelled biomolecule request; or biomolecule request and label request) and the system searches (603) the memory for storage identifiers that correspond to that particular request. When the appropriate dataset is retrieved, the processing module identifies one or more storage identifiers that correspond with the components of the labelled biomolecule reagent request (604). If more than one labelled biomolecule reagent request is inputted by a single user, the system may repeat the above until all storage identifiers from the user's requests are located and identified by the processor (605).

Systems are configured to output (606) the identified storage identifiers once the labelled biomolecule reagent request from the user has been processed. The output manager may display the storage identifiers on an electronic display or print the storage identifiers (607). The storage identifiers may also be communicated electronically (608), such as to a reagent preparatory apparatus or over the internet to a third party manufacturer.

In some embodiments, systems include a reagent preparatory apparatus for preparing the labelled biomolecule reagent that corresponds to the requested labelled biomolecule received by the input manager. The reagent preparatory apparatus is operatively coupled to the output manager and is configured to receive the identified storage identifiers (e.g., labelled biomolecule storage identifier, biomolecule storage identifier, label storage identifier, reactive linker storage identifier) and produce the labelled biomolecule reagent according to the received storage identifiers. In these embodiments, the reagent preparatory apparatus may be in communication with the output manager locally, such as through a cable or local area network or may be in a remote location and connected to the output manager through a wide-area network or through the internet. To facilitate connectivity between the reagent preparatory apparatus and the output manager, systems may include any suitable connectivity protocols, such as a cables, transmitters, relay stations, network servers, network interface cards, Ethernet modems, telephone network connections as well as satellite network connections. In certain embodiments, the reagent preparatory apparatus includes a graphical user interface where the storage identifiers from the output manager are manually inputted into an input manager operatively coupled to the graphical user interface of the reagent preparatory apparatus.

In certain embodiments, the reagent preparatory apparatus is fully automated. By "fully automated" is meant that the reagent preparatory apparatus receives the identified storage identifiers from the output manager and prepares, formulates and packages the labelled biomolecule reagent with little to no human intervention or manual input into the subject systems. In certain embodiments, the subject systems are configured to prepare, purify and package the labelled biomolecule reagent from an activated biomolecule and activated label without any human intervention.

The reagent preparatory apparatus includes a sampling device that provides an activated biomolecule and an activated label to a contacting apparatus. The sampling device may be any convenient device in fluid communication with each source of activated biomolecule and activated label, such as for example, a high throughput sample changer having a plurality of reagent vials containing activated biomolecules and activated labels. The sampling device may also include microfluidic channels, syringes, needles, pipets, aspirators, among other sampling devices. The contacting apparatus may be any suitable apparatus which allows for an activated biomolecule to be contacted with an activated label. For example, in some embodiments, the contacting apparatus is a sample chamber (e.g., enclosed, sealed, airtight, open, plate, etc.). In other embodiments, the contacting apparatus is a microtube. In other embodiments, the contacting apparatus is a test tube. In yet other embodiments, the contacting apparatus is a glass flask (e.g., beaker, volumetric flask, Erlenmeyer flask, etc.). In still other embodiments, the contacting apparatus is a 96-well plate. In certain embodiments, the subject systems may further include a packaging unit configured to seal the produced labelled biomolecule reagent in the contacting apparatus (e.g., microtube, test tube, etc.). In other embodiments, the produced labelled biomolecule reagent is first characterized and further purified, diluted, concentrated or re-formulated before sealing in a container and packaged with the packaging unit.

The contacting apparatus may further include an agitator for mixing the combined activated biomolecule and activated label. The agitator may be any convenient agitator sufficient for mixing the subject compositions, including but not limited to vortexers, sonicators, shakers (e.g., manual, mechanical, or electrically powered shakers), rockers, oscillating plates, magnetic stirrers, static mixers, rotators, blenders, mixers, tumblers, orbital shakers, bubbles, microfluidic flow, among other agitating protocols.

In some embodiments, the reagent preparatory apparatus also includes a source of activated biomolecules and activated labels. The source may include a plurality of activated biomolecules and activated labels. In some instances, the reagent preparatory apparatus includes a source containing 5 or more different types of activated biomolecules, such as 10 or more, such as 100 or more, such as 250 or more, such as 500 or more and including 1000 or more different types of activated biomolecules. For example, the reagent preparatory apparatus may include a source containing 5 or more different types of activated antibody probes or activated oligonucleotide probes, such as 10 or more, such as 100 or more, such as 250 or more, such as 500 or more and including 1000 or more different types of activated antibody probes or activated oligonucleotide probes.

In some embodiments, the reagent preparatory apparatus includes a source containing 5 or more different types of activated labels, such as 10 or more, such as 15 or more, such as 25 or more, such as 50 or more and including 100 or more different types of activated labels. For example, the reagent preparatory apparatus may include a source containing 5 or more different types of activated fluorophores, such as 10 or more, such as 15 or more, such as 25 or more, such as 50 or more and including 100 or more different types of activated fluorophores.

The source of activated biomolecules and activated labels may be any suitable reservoir that is capable of storing and providing one or more type of activated biomolecule and activated label to the contacting apparatus. In one example, the source is a single high throughput reservoir that stores a plurality of different types of activated biomolecules and activated labels in separate, partitioned reagent chambers. In another example, the source of activated biomolecules and activated labels is a plurality of individual vials of each activated biomolecule and each activated label. In yet another example, the source of activated biomolecules and activated labels is a reservoir with pre-measured aliquots of each activated biomolecule and each activated label. For example, the reservoir may include pre-measured aliquots of each activated biomolecule and each activated label sufficient to prepare one or more labelled biomolecules, such as 2 or more, such as 5 or more, such as 10 or more, such as 25 or more, such as 100 or more, such as 500 or more and including 1000 or more labelled biomolecules. Depending on the particular design of reservoir containing the activated biomolecules and activated labels, the reagent preparatory apparatus may further include one or more inlets for delivering the activated biomolecules and activated labels to the contacting apparatus.

The reagent preparatory apparatus may also include one or more reagent purifiers. Reagent purification protocols of interest may include, but is not limited to size exclusion chromatography, ion exchange chromatography, filtration (e.g., membrane filters, size cut-off filtration), liquid-liquid extraction, passive dialysis, active dialysis, centrifugation, precipitation, among other purification protocols.

The reagent preparatory apparatus may also include a reagent analyzer. In certain embodiments, the sample analyzer may be mass cytometry, mass spectrometry (e.g., TOF mass spectrometry, inductively coupled plasma mass spectrometry), absorbance spectroscopy, fluorescence spectroscopy, volumetric analysis, conductivity analysis, nuclear magnetic resonance spectroscopy, infrared spectroscopy, UV-vis spectroscopy, colorimetry, elemental analysis, liquid chromatography-mass spectrometry or gas chromatography-mass spectrometry systems. For example, the apparatus may include analytical separation device such as a liquid chromatograph (LC), including a high performance liquid chromatograph (HPLC), fast protein liquid chromatography (FPLC) a micro- or nano-liquid chromatograph or an ultra high pressure liquid chromatograph (UHPLC) device, a capillary electrophoresis (CE), or a capillary electrophoresis chromatograph (CEC) apparatus. However, any manual or automated injection or dispensing pump system may be used. For instance, the subject sample may be applied to the LC-MS system by employing a nano- or micropump in certain embodiments. Mass spectrometer systems may be any convenient mass spectrometry system, which in general contains an ion source for ionizing a sample, a mass analyzer for separating ions, and a detector that detects the ions. In certain cases, the mass spectrometer may be a so-called "tandem" mass spectrometer that is capable of isolating precursor ions, fragmenting the precursor ions, and analyzing the fragmented precursor ions. The ion source may rely on any type of ionization method, including but not limited to electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof (to provide a so-called "multimode" ionization source). In one embodiment, the precursor ions may be made by EI, ESI or MALDI, and a selected precursor ion may be fragmented by collision or using photons to produce product ions that are subsequently analyzed. Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof. In one embodiment, the mass analyzer may be a sector, transmission quadrupole, or time-of-flight mass analyzer.

The reagent preparatory apparatus may also be configured to formulate the labelled biomolecule reagent with one or more excipients, such as a buffer, preservative, drying agent, etc. In certain embodiments, the reagent preparatory apparatus is configured to formulate the labelled biomolecule reagent with one or more buffers. Example buffers may include but are not limited to PBS (phosphate) buffer, acetate buffer, N,N-bis(2-hydroxyethyl)glycine (Bicine) buffer, 3-{[tris(hydroxymethyl)methyl]amino}propanesulfonic acid (TAPS) buffer, 2-(N-morpholino)ethanesulfonic acid (MES) buffer, citrate buffer, tris(hydroxymethyl)methylamine (Tris) buffer, N-tris(hydroxymethyl)methylglycine (Tricine) buffer, 3-[N-Tris(hydroxymethyl)methylamino]-2-hydroxypropanesulfonic Acid (TAPSO) buffer, 4-2-hydroxyethyl-1-piperazineethanesulfonic acid (HEPES) buffer, 2-{[tris(hydroxymethyl)methyl]amino}ethanesulfonic acid (TES) buffer, piperazine-N,N'-bis(2-ethanesulfonic acid) (PIPES) buffer, dimethylarsinic acid (Cacodylate) buffer, saline sodium citrate (SSC) buffer, 2(R)-2-(methylamino)succinic acid (succinic acid) buffer, potassium phosphate buffer, N-Cyclohexyl-2-aminoethanesulfonic acid (CHES) buffer, among other types of buffered solutions.

The reagent preparatory apparatus may also include a packing unit for packaging the labelled biomolecule reagent. In certain embodiments, the packaging unit may package the prepared labelled biomolecule reagent and prepare the labelled biomolecule reagent for shipping, such as by mail. In certain instances, the prepared labelled biomolecule reagent is dispensed into a container and sealed. In other instances, the labelled biomolecule reagent is dispensed into a container, sealed and further packaged such as in a pouch, bag, tube, vial, microtube or bottle. Where desired, the packaging may be sterile.

In certain embodiments, systems of interest include an on-demand standalone labelled biomolecule reagent dispensing station configured to: 1) receive one or more requests for a labelled biomolecule reagent; 2) prepare the requested labelled biomolecule reagent and 3) deliver the prepared labelled biomolecule reagent to the requestor (e.g., customer). For example, the standalone reagent dispensing station may be a self-vending machine that is configured to receive one or more labelled biomolecule reagent requests from a customer, prepare the requested labelled biomolecule and dispense the prepared labelled biomolecule to the customer on demand. Depending on the number of labelled biomolecule reagent requests and the amount of each labelled biomolecule reagents requested, standalone reagent dispensing stations of interest may prepare and dispense the labelled biomolecule to the requestor on demand in 10 seconds or more after input of the labelled biomolecule request, such as in 15 seconds or more, such as in 30 seconds or more, such as in 1 minute or more, such as in 5 minutes or more, such as in 10 minutes or more, such as in 15 minutes or more, such as in 30 minutes or more and including in 60 minutes or more, such as in 1.5 hours or more, such as in 2 hours or more, such as in 2.5 hours or more, such as in 3 hours or more, such as in 4 hours or more, such as in 5 hours or more, such as in 6 hours or more, such as in 8 hours or more, such as in 10 hours or more, such as in 12 hours or more, such as in 16 hours or more, such as in 18 hours or more and including in 24 hours or more. In some instances, the standalone reagent dispensing station is configured to prepare and dispense the labelled biomolecule to the requestor on demand in a duration that ranges from 5 seconds to 60 seconds, such as from 10 seconds to 50 seconds and including from 15 seconds to 45 seconds. In other instances, the standalone reagent dispensing station is configured to prepare and dispense the labelled biomolecule to the requestor on demand in a duration that ranges from 1 minute to 60 minutes, such as from 2 minutes to 55 minutes, such as from 5 minutes to 50 minutes, such as from 15 minutes to 45 minutes and including from 20 minutes to 40 minutes, for example preparing and dispensing the labelled biomolecule to the requestor in 30 minutes. In still other instances, the standalone reagent dispensing station is configured to prepare and dispense the labelled biomolecule to the requestor on demand in a duration that ranges from 0.5 hours to 24 hours, such as from 1 hour to 20 hours, such as from 1.5 hours to 18 hours, such as from 2 hours to 16 hours, such as from 2.5 hours to 12 hours, such as from 3 hours to 10 hours, such as from 3.5 hours to 8 hours and including from 4 hours to 6 hours.

In these embodiments, the subject standalone reagent dispensing stations may include the components for receiving a labelled biomolecule reagent request and preparing the requested labelled biomolecule reagent, as described above. For instance, the standalone labelled biomolecule reagent dispensing station may include an input module for receiving a request for a labelled biomolecule; a reagent preparatory apparatus; and a dispensing module for outputting a packaged labelled biomolecule. In these embodiments, the input module may include an input manager for receiving a request for a labelled biomolecule, a memory for storing a dataset having a plurality of storage identifiers that correspond to the one or more components of the labelled biomolecule reagent request (e.g., biomolecule, label, etc.), a processing module communicatively coupled to the memory and configured to identify a storage identifier from the dataset that corresponds to the components of the labelled biomolecule reagent request and an output manager for providing the identified storage identifiers. The standalone station also includes, as described above, a graphical user interface as well as user input devices for communicating the labelled biomolecule request to the input manager of the standalone dispensing station.

In embodiments, the output manager is communicatively coupled to the reagent preparatory apparatus in the standalone reagent dispensing station which is configured with one or more sources of biomolecules, labels, reactive linkers, activated biomolecules and activated labels and a contacting station for coupling an activated biomolecule and an activated label to produce the requested labelled biomolecule. In certain embodiments, the standalone reagent dispensing station includes a plurality of pre-synthesized labelled biomolecules and the standalone reagent dispensing station is configured to aliquot an amount of the pre-synthesized labelled biomolecule reagent into a container and dispense the labelled biomolecule reagent to the requestor.

The standalone labelled biomolecule reagent dispensing station also includes a dispensing module that is configured to provide a packaged labelled biomolecule reagent. In embodiments, the dispensing module may include a packaging unit for packaging the prepared labelled biomolecule reagent. In certain instances, the prepared labelled biomolecule reagent is dispensed into a container and sealed. In other instances, the labelled biomolecule reagent is dispensed into a container, sealed and further packaged such as in a pouch, bag, tube, vial, microtube or bottle. Where desired, the packaging may be sterile.

In certain embodiments, the standalone reagent dispensing station is fully automated, where a labelled biomolecule request is received and and the station prepares, purifies and packages the labelled biomolecule reagent with little to no human intervention or manual input into the subject systems apart from the labelled biomolecule request.

Methods for Preparing a Labelled Biomolecule Reagent

Aspects of the present disclosure also include methods for preparing a labelled biomolecule reagent. Methods according to certain embodiments include receiving a request for a labelled biomolecule reagent and preparing a labelled biomolecule. In other embodiments, methods include receiving a request for a labelled biomolecule reagent with one or more input managers as described above, identifying a storage identifier that corresponds with the labelled biomolecule reagent request; outputting the one or more identified storage identifiers and preparing the labelled biomolecule from the identified storage identifiers.

As discussed above, the labelled biomolecule reagent is a biological macromolecule that is coupled (e.g., covalently bonded) to a detectable marker. In some embodiments, methods include preparing a polypeptide coupled to a detectable marker, a nucleic acid coupled to a detectable marker, a polysaccharide coupled to a detectable marker, or a combination thereof. In one example, the biomolecule is an oligonucleotide, truncated or full-length DNA or RNA. In another example, the biomolecule is a polypeptide, protein, enzyme or antibody. In certain instances, the biomolecule is a biological probe having a specific binding domain sufficient to bind an analyte of interest. Specific binding domains of interest include, but are not limited to, antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'2 fragments, as well as molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

Labels of interest include detectable markers that are detectible based on, for example, fluorescence emission, fluorescence polarization, fluorescence lifetime, fluorescence wavelength, absorbance maxima, absorbance wavelength, Stokes shift, light scatter, mass, molecular mass, redox, acoustic, raman, magnetism, radio frequency, enzymatic reactions (including chemiluminescence and electrochemiluminescence) or combinations thereof. Labels of interest may include, but are not limited to fluorophores, chromophores, enzymes, redox labels, radiolabels, acoustic labels, Raman (SERS) tag, mass tag, isotope tag (e.g., isotopically pure rare earth element), magnetic particles, microparticles and nanoparticles.

Methods include receiving a request for a labelled biomolecule reagent. In embodiments of the present disclosure, the labelled biomolecule reagent request includes one or more of: 1) a labelled biomolecule request; and 2) a biomolecule request and a label request. In some instances, the biomolecule request is an activated biomolecule request where biomolecule is coupled to a reactive linker. In other instances, the label request is an activated label request where the label is coupled to a reactive linker. The labelled biomolecule reagent request may be received by any convenient communication protocol including, but not limited to, receiving the labelled biomolecule reagent request over the telephone, by facsimile, electronic mail or postal mail. In certain embodiments, the labelled biomolecule reagent request is communicated by inputting the labelled biomolecule reagent request into a graphical user interface on a computer, such as through an internet website.

One or more labelled biomolecule reagent requests may be received (simultaneously or sequentially), such as receiving 2 or more labelled biomolecule reagent requests, such as 5 or more, such as 10 or more and including receiving 25 or more labelled biomolecule reagent requests. Where the request for a labelled biomolecule reagent includes only a single component and is a labelled biomolecule request, methods may include receiving 2 or more labelled biomolecule requests, such as 5 or more, such as 10 or more and including 25 or more labelled biomolecule requests. Where the labelled biomolecule reagent request includes two components, such as a biomolecule request and a label request, methods may include receiving 2 or more biomolecule requests, such as 5 or more, such as 10 or more and including 25 or more biomolecule requests and configured to receive 2 or more label requests, such as 5 or more, such as 10 or more and including 25 or more label requests. In some instances, methods including receiving a labelled biomolecule reagent request that includes a single biomolecule request and single label request. In other instances, methods include receiving a labelled biomolecule reagent request that includes a single biomolecule request and a plurality of different label requests. In yet other instances, the methods include receiving a labelled biomolecule reagent request that includes a plurality of different biomolecule requests and a single label request. In still other instances, methods include receiving a labelled biomolecule reagent request that includes a plurality of different biomolecule requests and a plurality of different label requests.

The labelled biomolecule reagent requests may be received from a single user or a plurality of users, such as from 2 or more users, such as from 5 or more users, such as from 10 or more users, such as from 25 or more users and including receiving labelled biomolecule requests from 100 or more users.

In certain embodiments, methods include receiving a request for a labelled biomolecule reagent and inputting the request into a graphical user interface of an input manager (as described above) entered through. In other embodiments, the user making the labelled biomolecule reagent request inputs the request directly into the graphical user interface. The labelled biomolecule request, in these embodiments, may be entered into the graphical user interface and communicated to the input manager as a string of one or more characters (e.g., alphanumeric characters), symbols, images or other graphical representation(s) of the labelled biomolecule. In some instances, the request is a "shorthand" designation or other suitable identifier of the labelled biomolecule, biomolecule, label, activated biomolecule, activated label or reactive linker. For example, the request may include biomolecule name, label name, ascension number, sequence identification number, abbreviated probe sequence, chemical structure or Chemical Abstracts Service (CAS) registry number.

As described above, after the labelled biomolecule request is received by the input manager, a processing module of the subject systems identifies one or more storage identifiers from a dataset stored in memory that corresponds to the components of the received labelled biomolecule reagent request (e.g., a labelled biomolecule storage identifier, a biomolecule storage identifier, a label storage identifier, a reactive linker storage identifier, etc.) The storage identifiers that correspond to each component of the received labelled biomolecule reagent request is outputted by an output manager. In some instances, each labelled biomolecule storage identifier is displayed on a monitor. In other instances, the storage identifiers is outputted by printing in a machine (e.g., as a barcode) or human readable format. Where the labelled biomolecule reagent is prepared by a computer controlled reagent preparatory apparatus (as described in greater detail below), the output manager is operatively coupled to the reagent preparatory apparatus and each storage identifier may electronically communicated to the reagent preparatory apparatus, such as through an internet protocol, including but not limited to SQL, HTML or XML documents, email or other files, or data in other forms.

Depending on the number of labelled biomolecule requests received, one or more storage identifiers may be simultaneously outputted by the output manager, such as 2 or more, such as 3 or more, such as 3 or more, such as 5 or more, such as 10 or more, such as 25 or more, such as 100 or more and including outputting 500 or more storage identifiers. Each set of outputted storage identifiers may correspond with the labelled biomolecule requests from a single user or from a plurality of users.

In certain embodiments, the output manager organizes (e.g., groups together) storage identifiers based on a predetermined criteria before displaying or printing the storage identifiers. In one example, the output manager groups together all of the storage identifiers from a particular user. In another example, the output manager groups together all of the same labelled biomolecule storage identifiers. In yet another example, the output manager organizes the storage identifiers based on name or type of biomolecule (e.g., antibody, oligonucleotide). In still another example, the output manager organizes the storage identifiers based on the name or type of label (e.g., fluorescein, coumarin).

In some embodiments, methods include preparing a labelled biomolecule reagent according to the received request and/or the outputted storage identifiers. In some embodiments, preparing the labelled biomolecule reagent includes selecting an activated biomolecule and an activated label from a storage having a plurality of activated biomolecules and a plurality of activated labels. Each labelled biomolecule reagent may be prepared manually by one or more individuals, such as in a laboratory or may be prepared with a computer-controlled reagent preparatory apparatus (e.g., a high throughput preparatory system) as described above. In some instances, where the outputted storage identifier is a labelled biomolecule storage identifier, methods include retrieving the labelled biomolecule from a storage that corresponds to the outputted labelled biomolecule storage identifier. In these instances, methods may further include purifying the labelled biomolecule from the storage or adding one or more additional reagents (e.g., buffers, antioxidants, etc.) as desired. In other instances, the retrieved labelled biomolecule may be packaged and shipped to the user without further purification or additions to the composition.

In other embodiments, the labelled biomolecule is prepared by contacting an activated biomolecule that corresponds with the outputted biomolecule storage identifier with an activated label that corresponds with the outputted label storage identifier. Any convenient reaction protocol may be employed to mix the activated biomolecule with the activated label, so long as reaction is sufficient to form a covalent bond between the reactive linker of the activated biomolecule and the reactive linker of the activated label. Mixing, in certain embodiments, may include stirring the mixture with a magnetic stir bar or manually stirring the mixture as well as vortexing of agitating the mixture either manually (i.e., by hand) or mechanically (i.e., by a mechanically or electrically powered shaking device). The activated biomolecule and activated label are contacted for a duration sufficient to couple the activated biomolecule to the activated label, such as for 1 minute or longer, such as for 5 minutes or longer, such as for 10 minutes or longer and including for 30 minutes or longer.

As discussed above, the activated biomolecule and activated label each include a reactive linker which when carried out under appropriate conditions, react together to form chemical linkage, such as for example, an ionic bond (charge-charge interaction), a non-covalent bond (e.g., dipole-dipole or charge-dipole) or a covalent bond. In some embodiments, the reactive linker or moiety of the activated biomolecule reacts with the reactive linker or moiety of the activated label to produce an ionic bond. In other embodiments, the reactive linker or moiety of the activated biomolecule reacts with the reactive linker or moiety of the activated label to produce a non-covalent bond. In yet other embodiments, the reactive linker or moiety of the activated biomolecule reacts with the reactive linker or moiety of the activated label to produce a covalent bond. In certain embodiments, the reactive linker of the activated biomolecule and the reactive linker of the activated label react to produce a covalent bond. Any convenient protocol for forming a covalent bond between the reactive linker of the activated biomolecule and the reactive linker of the activated label may be employed, including but not limited to addition reactions, elimination reactions, substitution reactions, pericyclic reactions, photochemical reactions, redox reactions, radical reactions, reactions through a carbene intermediate, metathesis reaction, among other types of bond-forming reactions. In some embodiments, the activated biomolecule may be conjugated to the activated label through reactive linking chemistry such as where reactive linker pairs include, but is not limited to: maleimide/thiol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate—periodate/hydrazine or amine;

diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylate)/thiol and amine/BMPH (N-[β-Maleimidopropionic acid]hydrazide.TFA)/thiol; azide/triarylphosphine; nitrone/cyclooctyne; azide/tetrazine and formylbenzamide/hydrazino-nicotinamide.

After contacting the activated biomolecule and activated label for a duration sufficient to form a chemical linkage (e.g., covalent bond) between each respective reactive linker, the labelled biomolecule may be further purified, such as by microextraction, gel electrophoresis, liquid-liquid extraction, centrifugation, precipitation, passive or active dialysis, or solid phase chromatography, including but not limited to ion exchange chromatography, liquid chromatography employing a reverse phase stationary column, size exclusion chromatography, high performance liquid chromatography and preparatory thin layer chromatography, ultrafiltration (membrane filters with size cut offs), among other purification protocols.

Methods may also include analysis of the prepared labelled biomolecule reagent. By analyzed is meant characterizing the chemical composition of the labelled biomolecule reagent, including but not limited to the amount and types of compounds in the prepared reagent composition as well as any impurities present. Analysis of the prepared labelled biomolecule reagent may be conducted using any convenient protocol, such as for example by physical measurements (e.g., mass analysis, density analysis, volumetric analysis, etc.) mass spectrometry (e.g., TOF mass spectrometry, inductively coupled plasma mass spectrometry), mass cytometry, absorbance spectroscopy, fluorescence spectroscopy, conductivity analysis, infrared spectroscopy, UV-vis spectroscopy, colorimetry, elemental analysis and nuclear magnetic resonance spectroscopy. In some instances, analysis of the labelled biomolecule is conducted by mass spectrometry. In some instances, analysis of the labelled biomolecule is conducted by fluorescence spectroscopy. In some instances, analysis of the labelled biomolecule is conducted by gas chromatography. In some instances, analysis of the labelled biomolecule is conducted by liquid chromatography. In some instances, analysis of the labelled biomolecule is conducted by elemental analysis. In certain embodiments, analysis of the labelled biomolecule reagent is conducted by gas chromatography-mass spectrometry. In other embodiments, analysis of the labelled biomolecule reagent is conducted by liquid chromatography-mass spectrometry. For example, the apparatus may include analytical separation device such as a liquid chromatograph (LC), including a high performance liquid chromatograph (HPLC), fast protein liquid chromatography (FPLC) a micro- or nano-liquid chromatograph or an ultra high pressure liquid chromatograph (UHPLC) device, a capillary electrophoresis (CE), or a capillary electrophoresis chromatograph (CEC) apparatus. However, any manual or automated injection or dispensing pump system may be used. For instance, the subject sample may be applied to the LC-MS system by employing a nano- or micropump in certain embodiments. Mass spectrometer systems may be any convenient mass spectrometry system, which in general contains an ion source for ionizing a sample, a mass analyzer for separating ions, and a detector that detects the ions. In certain cases, the mass spectrometer may be a so-called "tandem" mass spectrometer that is capable of isolating precursor ions, fragmenting the precursor ions, and analyzing the fragmented precursor ions. The ion source may rely on any type of ionization method, including but not limited to electrospray ionization (ESI), atmospheric pressure chemical ionization (APOI), electron impact (EI), atmospheric pressure photoionization (APPI), matrix-assisted laser desorption ionization (MALDI) or inductively coupled plasma (ICP) ionization, for example, or any combination thereof (to provide a so-called "multi-mode" ionization source). In one embodiment, the precursor ions may be made by EI, ESI or MALDI, and a selected precursor ion may be fragmented by collision or using photons to produce product ions that are subsequently analyzed. Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof. In one embodiment, the mass analyzer may be a sector, transmission quadrupole, or time-of-flight mass analyzer.

After preparation (as well as purification and analysis, where desired) of the labelled biomolecule reagent, each prepared labelled biomolecule reagent may be loaded into a container for packaging and delivery in accordance with the labelled biomolecule request (i.e., transported to the user originating the labelled biomolecule request). In certain embodiments, the labelled biomolecule reagent is prepared and delivered to the user in the container used to contact the activated biomolecule with the activated label. For example, the labelled biomolecule reagent may be packaged and delivered in the microtube used to contact the activated biomolecule with the activated label. Methods may also include delivering the packaged labelled biomolecule reagent to the requestor, such as by mail.

The prepared labelled biomolecule reagent may be packaged with other components, such as for using or storing the labelled biomolecule reagent, including but not limited to buffers, syringes, needles, micropipets, glass slides, desiccants, etc. In addition, the packaged labelled biomolecule reagent may further include instructions for storing and using the labelled biomolecule reagent. The instructions may be recorded on a suitable recording medium, such as printed on paper or plastic, etc. The instructions may be present as a package insert, such as in the labeling of the container. In other embodiments, the instructions may be present as electronic storage data file present on a suitable computer readable storage medium, e.g. CD-ROM, SD card, USB drive etc. In yet other embodiments, the actual instructions are not present in the package, but means for obtaining the instructions from a remote source, e.g. via the internet, are provided. An example of this embodiment is a paper or plastic insert having a web address where the instructions can be viewed and/or from which the instructions can be downloaded.

Methods for Requesting and Receiving a Labelled Biomolecule Reagent

Aspects of the present disclosure also include methods for requesting and receiving a labelled biomolecule reagent. Methods according to certain embodiments include communicating a request for a labelled biomolecule reagent, the labelled biomolecule request including one or more of: 1) a labelled biomolecule request; and 2) a biomolecule request and a label request and receiving a labelled biomolecule reagent that includes a biomolecule covalently bonded to a label. In practicing the subject methods, the labelled biomolecule request may be communicated by any convenient communication protocol including, but not limited to, communicating the labelled biomolecule request over the telephone, by facsimile, electronic mail or postal mail. In certain embodiments, the labelled biomolecule request is communicated by inputting the labelled biomolecule reagent request into a graphical user interface on a computer, such as on an internet website.

One or more labelled biomolecule reagent requests may be communicated, such as communicating 2 or more labelled biomolecule reagent requests, such as 5 or more, such as 10 or more and including communicating 25 or more labelled biomolecule reagent requests. In some embodiments, methods include communicating a labelled biomolecule reagent request that includes a single biomolecule request and a single label request. In other embodiments, the labelled biomolecule reagent request includes a single biomolecule request and a plurality of label requests. In yet other embodiments, the labelled biomolecule reagent request includes a plurality of biomolecule requests and a single label request. In still other embodiments, the labelled biomolecule request includes a plurality of biomolecule requests and a plurality of label requests. In certain embodiments, the labelled biomolecule reagent request includes one or more labelled biomolecule requests.

In certain embodiments, the labelled biomolecule reagent request is communicated by inputting the request on a graphical user interface, such as on an internet website. The graphical user interface may display all or part of a database (e.g., catalog) of labelled biomolecules, activated biomolecules, biomolecules, activated labels, labels and reactive linkers. Each category from the database may be displayed as a list, drop-down menu or other configuration. The labelled biomolecule reagent request may be entered by inputting information or data associated with the biomolecule and the label into appropriate text fields or by selecting check boxes or selecting one or more items from a drop-down menu, or by using a combination thereof.

In one example, a labelled biomolecule reagent request is inputted into the graphical user interface by selecting a labelled biomolecule from a drop-down menu. In another example, a labelled biomolecule reagent request is inputted into the graphical user interface by selecting one or more biomolecules from a first drop-down menu and one or more labels from a second drop-down menu. In yet another example, a labelled biomolecule reagent request is inputted into the graphical user interface by selecting one or more biomolecules from a first drop-down menu, one or more labels from a second drop-down menu and one or more reactive linkers from a third drop-down menu.

To input a labelled biomolecule reagent request, information or data associated with a particular labelled biomolecule, biomolecule or label is entered onto the graphical user interface. The information or data entered may be a string of one or more characters (e.g., alphanumeric characters), symbols, images or other graphical representation(s) of the labelled biomolecule. In some instances, a "shorthand" designation or other suitable identifier of the labelled biomolecule, biomolecule, label, activated biomolecule, activated label or reactive linker are entered. For example, biomolecule name, label name, ascension number, sequence identification number, abbreviated probe sequence, chemical structure or Chemical Abstracts Service (CAS) registry number may be entered.

In some embodiments, the labelled biomolecule reagent includes a polypeptide and the request may include information such as polypeptide name, protein name, enzyme name, antibody name or the name of protein, enzyme or antibody fragments thereof, polypeptides derived from specific biological fluids (e.g., blood, mucus, lymphatic fluid, synovial fluid, cerebrospinal fluid, saliva, bronchoalveolar lavage, amniotic fluid, amniotic cord blood, urine, vaginal fluid and semen), polypeptides derived from specific species (e.g., mouse monoclonal antibodies) as well as amino acid sequence identification number. In certain embodiments, the labelled biomolecule reagent includes a biological probe and the request includes information or data associated with a specific binding domain.

In other embodiments, the labelled biomolecule reagent includes a nucleic acid and the request may include information such as oligonucleotide name, oligonucleotides identified by gene name, oligonucleotides identified by accession number, oligonucleotides of genes from specific species (e.g., mouse, human), oligonucleotides of genes associated with specific tissues (e.g., liver, brain, cardiac), oligonucleotides of genes associate with specific physiological functions (e.g., apoptosis, stress response), oligonucleotides of genes associated with specific disease states (e.g., cancer, cardiovascular disease) as well as nucleotide sequence identification number.

In certain embodiments, methods for requesting a labelled biomolecule further include completing a questionnaire or survey related to the labelled biomolecule request. In these embodiments, the requestor of the labelled biomolecule is prompted with a series of questions, or in the form of a questionnaire or survey related to the labelled biomolecule request. For example, the questionnaire or survey may include one question related to the labelled biomolecule request, such as 2 or more questions, such as 3 or more questions, such as 4 or more questions and including 5 or more questions related to the labelled biomolecule request. The content of questionnaire or survey may vary depending on the information that is desired. For instance, questions in the questionnaire or survey may include, but are not limited to, requests to provide the contents of a requestor's reagent inventory, the types of experiments being conducted with the labelled biomolecule as well as the timing of the use of the labelled biomolecule reagent. The questionnaire may also include one or more open text fields for inputting. For example, the questionnaire may be an open text feedback form.

In some embodiments, methods include prompting the requestor to complete the series of questions or survey before the labelled biomolecule request is communicated (e.g., inputted into the graphical user interface). In other embodiments, methods include prompting the requestor to complete the series of questions or survey after the labelled biomolecule request is completed. In still other embodiments, the requestor may be prompted with questions related to the labelled biomolecule request concurrently with communicating the labelled biomolecule request. For instance, methods may include prompting the requestor with a question about the specific use (e.g., experiments being conducted) of the labelled biomolecule when communicating the labelled biomolecule request.

As described above, the completed series of questions or survey may be used by the design platform to provide a recommendation for one or more labelled biomolecule, biomolecule, activated biomolecule, label, activated label or reactive linker. For example, the answers to the questions or survey may be used by the design platform to recommend a labelled biomolecule, biomolecule, activated biomolecule, label, activated label or reactive linker that is best suited for use with a particular analytical instrument (e.g., flow cytometer, fluorescence spectrometer) or that is best suited for the intended application of the labelled biomolecule. The design platform, in certain embodiments, is configured to use the answers to the completed series of questions or surveys to provide a recommendation for a labelled biomolecule, biomolecule, activated biomolecule, label, activated label or reactive linker based on the target density (e.g., antigen density on a cell)

The answers to the series of questions or survey may be communicated using the same or different protocol as used to communicate the labelled biomolecule request (e.g., telephone, facsimile, email, graphical user interface at a stand-alone station, graphical user interface through the internet). For example, where the labelled biomolecule is request is communicated through a graphical user interface through the internet, answers to the series of questions may also be inputted through the graphical user interface, such as with drop down menus or text fields.

Methods according to embodiments of the present disclosure also include receiving the labelled biomolecule reagent. The labelled biomolecule reagent may be received loaded in a container and may be packaged with one or more ancillary components, such as for using or storing the subject composition. In certain embodiments, the labelled biomolecule reagent is received with buffers, syringes, needles, micropipets, glass slides, desiccants, etc. The packaged labelled biomolecule reagent may also be received with instructions for storing and using the labelled biomolecule reagent, such as instructions printed on paper, plastic or on a computer readable medium (e.g., CD-ROM, SD-card, USB drive) or as an insert providing instructions for retrieving instructions for storing and using the subject compositions from a remote source, such as on the internet.

Storage Containing a Plurality of Activated Biomolecules and a Plurality of Activated Labels Aspects of the disclosure also include a storage containing a plurality of activated biomolecules and a plurality of activated labels. As discussed in detail above, the subject labelled biomolecule reagents are prepared by contacting an activated biomolecule with an activated label. In some embodiments, the activated biomolecules in the storage are polypeptides, nucleic acids, polypeptides or a combination thereof that are coupled to a reactive linker. In certain instances, the activated biomolecules in the storage are biological probes coupled to a reactive linker where the probe includes a specific binding domain for an analyte of interest, such as antibody binding agents, proteins, peptides, haptens, nucleic acids, etc. Activated labels are marker compounds that may be detectable based on, for example, fluorescence emission, absorbance, fluorescence polarization, fluorescence lifetime, fluorescence wavelength, absorbance maxima, absorbance wavelength, Stokes shift, light scatter, mass, molecular mass, redox, acoustic, raman, magnetism, radio frequency, enzymatic reactions (including chemiluminescence and electro-chemiluminescence) or combinations thereof. For example, the label may be a fluorophore, chromophore, enzyme, redox label, radiolabels, acoustic label, Raman (SERS) tag, mass tag, isotope tag (e.g., isotopically pure rare earth element), magnetic particle, microparticle as well as a nanoparticle.

In certain embodiments, activated labels in storage are fluorophores coupled to a reactive linker. Fluorophores of interest may include, but are not limited to, dyes suitable for use in analytical applications (e.g., flow cytometry, imaging, etc.), such as an acridine dye, anthraquinone dyes, arylmethane dyes, diarylmethane dyes (e.g., diphenyl methane dyes), chlorophyll containing dyes, triarylmethane dyes (e.g., triphenylmethane dyes), azo dyes, diazonium dyes, nitro dyes, nitroso dyes, phthalocyanine dyes, cyanine dyes, asymmetric cyanine dyes, quinon-imine dyes, azine dyes, eurhodin dyes, safranin dyes, indamins, indophenol dyes, fluorine dyes, oxazine dye, oxazone dyes, thiazine dyes, thiazole dyes, xanthene dyes, fluorene dyes, pyronin dyes, fluorine dyes, rhodamine dyes, phenanthridine dyes, as well as dyes combining two or more dyes (e.g., in tandem) as well as polymeric dyes having one or more monomeric dye units, as well as mixtures of two or more dyes thereof. For example, the fluorophore may be 4-acetamido-4'-isothiocyanatostilbene-2,2'disulfonic acid; acridine and derivatives such as acridine, acridine orange, acrindine yellow, acridine red, and acridine isothiocyanate; allophycocyanin, phycoerythrin, peridinin-chlorophyll protein, 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo) benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; dye-conjugated polymers (i.e., polymer-attached dyes) such as fluorescein isothiocyanate-dextran as well as dyes combining two or more of the aforementioned dyes (e.g., in tandem), polymeric dyes having one or more monomeric dye units and mixtures of two or more of the aforementioned dyes thereof.

In some instances, the fluorophore (i.e., dye) is a fluorescent polymeric dye. Fluorescent polymeric dyes that find use in the subject methods and systems are varied. In some instances of the method, the polymeric dye includes a conjugated polymer. Conjugated polymers (CPs) are characterized by a delocalized electronic structure which includes a backbone of alternating unsaturated bonds (e.g., double and/or triple bonds) and saturated (e.g., single bonds) bonds, where π-electrons can move from one bond to the other. As such, the conjugated backbone may impart an extended linear structure on the polymeric dye, with limited bond angles between repeat units of the polymer. For example, proteins and nucleic acids, although also polymeric, in some cases do not form extended-rod structures but rather fold into higher-order three-dimensional shapes. In addition, CPs may form "rigid-rod" polymer backbones and experience a limited twist (e.g., torsion) angle between monomer repeat units along the polymer backbone chain. In some instances, the polymeric dye includes a CP that has a rigid rod structure. As summarized above, the structural characteristics of the polymeric dyes can have an effect on the fluorescence properties of the molecules.

Any convenient polymeric dye may be utilized in the subject methods and systems. In some instances, a polymeric dye is a multichromophore that has a structure capable of harvesting light to amplify the fluorescent output of a fluorophore. In some instances, the polymeric dye is capable of harvesting light and efficiently converting it to emitted light at a longer wavelength. In some cases, the polymeric dye has a light-harvesting multichromophore system that can efficiently transfer energy to nearby luminescent species (e.g., a "signaling chromophore"). Mechanisms for energy transfer include, for example, resonant energy transfer (e.g., Forster (or fluorescence) resonance energy transfer, FRET), quantum charge exchange (Dexter energy transfer) and the like. In some instances, these energy transfer mechanisms are relatively short range; that is, close proximity of the light harvesting multichromophore system to the signaling chromophore provides for efficient energy transfer. Under conditions for efficient energy transfer, amplification of the emission from the signaling chromophore occurs when the number of individual chromophores in the light harvesting multichromophore system is large; that is, the emission from the signaling chromophore is more intense when the incident light (the "excitation light") is at a wavelength which is absorbed by the light harvesting multichromophore system than when the signaling chromophore is directly excited by the pump light.

The multichromophore may be a conjugated polymer. Conjugated polymers (CPs) are characterized by a delocalized electronic structure and can be used as highly responsive optical reporters for chemical and biological targets. Because the effective conjugation length is substantially shorter than the length of the polymer chain, the backbone contains a large number of conjugated segments in close proximity. Thus, conjugated polymers are efficient for light harvesting and enable optical amplification via energy transfer.

In some instances the polymer may be used as a direct fluorescent reporter, for example fluorescent polymers having high extinction coefficients, high brightness, etc. In some instances, the polymer may be used as an strong chromophore where the color or optical density is used as an indicator.

Polymeric dyes of interest include, but are not limited to, those dyes described by Gaylord et al. in US Publication Nos. 20040142344, 20080293164, 20080064042, 20100136702, 20110256549, 20120028828, 20120252986 and 20130190193 the disclosures of which are herein incorporated by reference in their entirety; and Gaylord et al., J. Am. Chem. Soc., 2001, 123 (26), pp 6417-6418; Feng et al., Chem. Soc. Rev., 2010, 39, 2411-2419; and Traina et al., J. Am. Chem. Soc., 2011, 133 (32), pp 12600-12607, the disclosures of which are herein incorporated by reference in their entirety.

In some embodiments, the polymeric dye includes a conjugated polymer including a plurality of first optically active units forming a conjugated system, having a first absorption wavelength (e.g., as described herein) at which the first optically active units absorbs light to form an excited state. The conjugated polymer (CP) may be polycationic, polyanionic and/or a charge-neutral conjugated polymer.

The CPs may be water soluble for use in biological samples. Any convenient substituent groups may be included in the polymeric dyes to provide for increased water-solubility, such as a hydrophilic substituent group, e.g., a hydrophilic polymer, or a charged substituent group, e.g., groups that are positively or negatively charged in an aqueous solution, e.g., under physiological conditions. Any convenient water-soluble groups (WSGs) may be utilized in the subject light harvesting multichromophores. The term "water-soluble group" refers to a functional group that is well solvated in aqueous environments and that imparts improved water solubility to the molecules to which it is attached. In some embodiments, a WSG increases the solubility of the multichromophore in a predominantly aqueous solution (e.g., as described herein), as compared to a multichromophore which lacks the WSG. The water soluble groups may be any convenient hydrophilic group that is well solvated in aqueous environments. In some cases, the hydrophilic water soluble group is charged, e.g., positively or negatively charged or zwitterionic. In certain cases, the hydrophilic water soluble group is a neutral hydrophilic group. In some embodiments, the WSG is a hydrophilic polymer, e.g., a polyethylene glycol, a cellulose, a chitosan, or a derivative thereof.

As used herein, the terms "polyethylene oxide", "PEO", "polyethylene glycol" and "PEG" are used interchangeably and refer to a polymer including a chain described by the formula —($CH_2$—$CH_2$—O—)$_n$- or a derivative thereof. In some embodiments, "n" is 5000 or less, such as 1000 or less, 500 or less, 200 or less, 100 or less, 50 or less, 40 or less, 30 or less, 20 or less, 15 or less, such as 5 to 15, or 10 to 15. It is understood that the PEG polymer may be of any convenient length and may include a variety of terminal groups, including but not limited to, alkyl, aryl, hydroxyl, amino, acyl, acyloxy, and amido terminal groups. Functionalized PEGs that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165. Water soluble groups of interest include, but are not limited to, carboxylate, phosphonate, phosphate, sulfonate, sulfate, sulfinate, ester, polyethylene glycols (PEG) and modified PEGs, hydroxyl, amine, ammonium, guanidinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —$SO_3$M', —$PO_3$M', —$NR_3^+$, Y', ($CH_2CH_2O$)$_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —($CH_2CH_2O$)$_{yy}$ $CH_2CH_2XR^{YY}$, —($CH_2CH_2O$)$_{yy}$$CH_2CH_2X$—, —X($CH_2CH_2O$)$_{yy}$$CH_2CH_2$—, glycol, and polyethylene glycol, wherein yy is selected from 1 to 1000, X is selected from O, S, and $NR^{ZZ}$, and $R^{ZZ}$ and $R^{YY}$ are independently selected from H and C1-3 alkyl.

The polymeric dye may have any convenient length. In some cases, the particular number of monomeric repeat units or segments of the polymeric dye may fall within the range of 2 to 500,000, such as 2 to 100,000, 2 to 30,000, 2 to 10,000, 2 to 3,000 or 2 to 1,000 units or segments, or such as 100 to 100,000, 200 to 100,000, or 500 to 50,000 units or segments. In certain instances, the number of monomeric repeat units or segments of the polymeric dye is within the range of 2 to 1000 units or segments, such as from 2 to 750 units or segments, such as from 2 to 500 units or segments, such as from 2 to 250 units or segment, such as from 2 to 150 units or segment, such as from 2 to 100 units or segments, such as from 2 to 75 units or segments, such as from 2 to 50 units or segments and including from 2 to 25 units or segments.

The polymeric dyes may be of any convenient molecular weight (MW). In some cases, the MW of the polymeric dye may be expressed as an average molecular weight. In some instances, the polymeric dye has an average molecular weight of from 500 to 500,000, such as from 1,000 to 100,000, from 2,000 to 100,000, from 10,000 to 100,000 or even an average molecular weight of from 50,000 to 100,000. In certain embodiments, the polymeric dye has an average molecular weight of 70,000.

The polymeric dye may have one or more desirable spectroscopic properties, such as a particular absorption maximum wavelength, a particular emission maximum wavelength, extinction coefficient, quantum yield, and the like.

In some embodiments, the polymeric dye has an absorption curve between 280 and 850 nm. In certain embodiments, the polymeric dye has an absorption maximum in the range 280 and 850 nm. In some embodiments, the polymeric dye absorbs incident light having a wavelength in the range between 280 and 850 nm, where specific examples of absorption maxima of interest include, but are not limited to: 348 nm, 355 nm, 405 nm, 407 nm, 445 nm, 488 nm, 640 nm and 652 nm. In some instances, the polymeric dye has an absorption maximum wavelength in a range selected from the group consisting of 280-310 nm, 305-325 nm, 320-350 nm, 340-375 nm, 370-425 nm, 400-450 nm, 440-500 nm, 475-550 nm, 525-625 nm, 625-675 nm and 650-750 nm. In certain embodiments, the polymeric dye has an absorption maximum wavelength of 348 nm. In some instances, the polymeric dye has an absorption maximum wavelength of 355 nm. In some instances, the polymeric dye has an absorption maximum wavelength of 405 nm. In some instances, the polymeric dye has an absorption maximum wavelength of 407 nm. In some instances, the polymeric dye has an absorption maximum wavelength of 445 nm. In some instances, the polymeric dye has an absorption maximum wavelength of 488 nm. In some instances, the polymeric dye has an absorption maximum wavelength of 640 nm. In some instances, the polymeric dye has an absorption maximum wavelength of 652 nm.

In some embodiments, the polymeric dye has an emission maximum wavelength ranging from 400 to 850 nm, such as 415 to 800 nm, where specific examples of emission maxima of interest include, but are not limited to: 395 nm, 421 nm, 445 nm, 448 nm, 452 nm, 478 nm, 480 nm, 485 nm, 491 nm, 496 nm, 500 nm, 510 nm, 515 nm, 519 nm, 520 nm, 563 nm, 570 nm, 578 nm, 602 nm, 612 nm, 650 nm, 661 nm, 667 nm, 668 nm, 678 nm, 695 nm, 702 nm, 711 nm, 719 nm, 737 nm, 785 nm, 786 nm, 805 nm. In some instances, the polymeric dye has an emission maximum wavelength in a range selected from the group consisting of 380-400 nm, 410-430 nm, 470-490 nm, 490-510 nm, 500-520 nm, 560-580 nm, 570-595 nm, 590-610 nm, 610-650 nm, 640-660 nm, 650-700 nm, 700-720 nm, 710-750 nm, 740-780 nm and 775-795 nm. In certain embodiments, the polymeric dye has an emission maximum of 395 nm. In some instances, the polymeric dye has an emission maximum wavelength of 421 nm. In some instances, the polymeric dye has an emission maximum wavelength of 478 nm. In some instances, the polymeric dye has an emission maximum wavelength of 480 nm. In some instances, the polymeric dye has an emission maximum wavelength of 485 nm. In some instances, the polymeric dye has an emission maximum wavelength of 496 nm. In some instances, the polymeric dye has an emission maximum wavelength of 510 nm. In some cases, the polymeric dye has an emission maximum wavelength of 570 nm. In certain embodiments, the polymeric dye has an emission maximum wavelength of 602 nm. In some instances, the polymeric dye has an emission maximum wavelength of 650 nm. In certain cases, the polymeric dye has an emission maximum wavelength of 711 nm. In some instances, the polymeric dye has an emission maximum wavelength of 737 nm. In some instances, the polymeric dye has an emission maximum wavelength of 750 nm. In some embodiments, the polymeric dye has an emission maximum wavelength of 786 nm. In certain instances, the polymeric dye has an emission maximum wavelength of 421 nm±5 nm. In some embodiments, the polymeric dye has an emission maximum wavelength of 510 nm±5 nm. In certain instances, the polymeric dye has an emission maximum wavelength of 570 nm±5 nm. In some instances, the polymeric dye has an emission maximum wavelength of 602 nm±5 nm. In some embodiments, the polymeric dye has an emission maximum wavelength of 650 nm±5 nm. In certain instances, the polymeric dye has an emission maximum wavelength of 711 nm±5 nm. In some cases, the polymeric dye has an emission maximum wavelength of 786 nm±5 nm. In certain embodiments, the polymeric dye has an emission maximum selected from the group consisting of 421 nm, 510 nm, 570 nm, 602 nm, 650 nm, 711 nm and 786 nm.

In some instances, the polymeric dye has an extinction coefficient of $1\times10^6$ $cm^{-1}M^{-1}$ or more, such as $2\times10^6$ $cm^{-1}M^{-1}$ or more, $2.5\times10^6$ $cm^{-1}M^{-1}$ or more, $3\times10^6$ $cm^{-1}M^{-1}$ or more, $4\times10^6$ $cm^{-1}M^{-1}$ or more, $5\times10^6$ $cm^{-1}M^{-1}$ or more, $6\times10^6$ $cm^{-1}M^{-1}$ or more, $7\times10^6$ $cm^{-1}M^{-1}$ or more, or $8\times10^6$ $cm^{-1}M^{-1}$ or more. In certain embodiments, the polymeric dye has a quantum yield of 0.05 or more, such as 0.1 or more, 0.15 or more, 0.2 or more, 0.25 or more, 0.3 or more, 0.35 or more, 0.4 or more, 0.45 or more, 0.5 or more, 0.6 or more, 0.7 or more, 0.8 or more, 0.9 or more, 0.95 or more, 0.99 or more and including 0.999 or more. For example, the quantum yield of polymeric dyes of interest may range from 0.05 to 1, such as from 0.1 to 0.95, such as from 0.15 to 0.9, such as from 0.2 to 0.85, such as from 0.25 to 0.75, such as from 0.3 to 0.7 and including a quantum yield of from 0.4 to 0.6. In certain cases, the polymeric dye has a quantum yield of 0.1 or more. In certain cases, the polymeric dye has a quantum yield of 0.3 or more. In certain cases, the polymeric dye has a quantum yield of 0.5 or more. In certain cases, the polymeric dye has a quantum yield of 0.6 or more. In certain cases, the polymeric dye has a quantum yield of 0.7 or more. In certain cases, the polymeric dye has a quantum yield of 0.8 or more. In certain cases, the polymeric dye has a quantum yield of 0.9 or more. In certain cases, the polymeric dye has a quantum yield of 0.95 or more. In some embodiments, the polymeric dye has an extinction coefficient of $1\times10^6$ or more and a quantum yield of 0.3 or more. In some embodiments, the polymeric dye has an extinction coefficient of $2\times10^6$ or more and a quantum yield of 0.5 or more.

In embodiments, the activated biomolecules and activated labels for preparing the labelled biomolecule reagent in accordance with the labelled biomolecule reagent request are obtained from the storage. The storage may have 10 or more different activated biomolecules, such as 25 or more, such as 50 or more, such as 100 or more, such as 250 or more, such as 500 or more and including 1000 or more activated biomolecules. In one example, the storage includes 10 or more different activated oligonucleotides, such as 25 or more, such as 50 or more, such as 100 or more, such as 250 or more, such as 500 or more and including 1000 or more activated oligonucleotides. In another example the storage includes 10 or more different activated polypeptides, such as 25 or more, such as 50 or more, such as 100 or more, such as 250 or more, such as 500 or more and including 1000 or more activated polypeptides. The storage may also include 10 or more different activated labels, such as 15 or more, such as 20 or more, such as 30 or more, such as 40 or more and including 50 or more different activated labels.

Each of the plurality of activated biomolecules and activated labels may be present in the storage in any suitable container capable of storing and providing the activated biomolecule or activated label when desired. In some embodiments, the plurality of different activated biomolecules and plurality of different activated labels are stored in a single reservoir partitioned into separate reagent chambers. In other embodiments, each of the plurality of different activated biomolecules and plurality of different activated labels are stored in individual containers (e.g., bottles, jugs, etc.) In yet other embodiments, each of the plurality of different activated biomolecules and plurality of different activated labels are stored in a plurality of vials, where each vial includes pre-measured aliquots of each activated biomolecule and each activated label. Each container in the storage may also include a label identifying the components of the activated biomolecule or activated label (e.g., name, structure, CAS registry number, ascension number, probe sequence, etc. of the biomolecule, label and reactive linker). The label may also include one or more machine readable components such as a Quick Response (QR) code or a bar code.

In some embodiments, the storage also includes a database of available activated biomolecules and activated labels. The database may be a printed catalog in paper or electronic form or may be a searchable electronic database, such as searchable by keyword, chemistry structure, ascension number, monomer sequence (e.g., amino acid or nucleotide sequence) or by CAS chemical registry number.

Utility

The subject systems and methods find use in preparing complex biological reagents (e.g., biological macromolecules coupled to detectable markers)—a process that is generally time consuming, financially inefficient and extraordinarily labor intensive when conducted on a large scale. The present disclosure provides a fast, efficient and highly scalable process for delivering high quality and performance specific products across a wide range of biomolecule and detectable label portfolios.

The systems and methods described herein also provide a unique and new way to request and provide customized biological reagents. In addition being able to choose pre-synthesized reagents from an extensive database (e.g., an online database), the subject systems and methods provide for user customization, where the user can create any desired labelled biomolecule on-demand. By simply choosing a biological macromolecule and a detectable marker on an easy-to-use graphical interface, a user can request any labelled biomolecule, which are used in a variety of different research applications and in medical diagnosis.

The present disclosure also provides access to large portfolios of complex biological reagents that are not possible when prepared by small scale synthesis. The subject systems and methods are scalable facilitating the preparation, on-demand, of thousands of different combinations of biomolecules and detectable markers. In certain embodiments, the subject systems provide fully automated protocols so that the preparation of customized detectable biomolecule probes requires little, if any human input.

The present disclosure also finds use in applications where cell analysis from a biological sample may be desired for research, laboratory testing or for use in therapy. In some embodiments, the subject methods and systems may facilitate analysis of cells obtained from fluidic or tissue samples such as specimens for diseases such as cancer. Methods and systems of the present disclosure also allow for analyzing cells from a biological sample (e.g., organ, tissue, tissue fragment, fluid) with enhanced efficiency and low cost as compared to using probe compositions synthesized de novo.

Notwithstanding the appended clauses, the disclosure set forth herein is also defined by the following clauses:

1. A system for use in preparing a labelled biomolecule reagent, the system comprising:
   an input manager for receiving a request for a labelled biomolecule reagent;
   a memory for storing a dataset comprising a plurality of labelled biomolecule storage identifiers;
   a processing module communicatively coupled to the memory and configured to identify one or more labelled biomolecule storage identifiers from the dataset that corresponds to the components of the labelled biomolecule reagent request;
   an output manager for providing the identified labelled biomolecule storage identifiers.
2. The system of clause 1, wherein the request for a labelled biomolecule reagent comprises a biomolecule request and a label request.
3. The system of clause 2, wherein the memory comprises a first dataset comprising a plurality of biomolecule storage identifiers for a plurality of activated biomolecules and a second dataset comprising a plurality of label storage identifiers for a plurality of activated labels.
4. The system of any one of clauses 1 to 3, wherein the output manager is operatively coupled to a communication component configured to display the identified labelled biomolecule storage identifiers.
5. The system of clause 4, wherein the communication component is an electronic display.
6. The system of clause 4, wherein the communication component is a printer.
7. The system of any one of clauses 1 to 6, wherein the input manager is operatively coupled to a graphical user interface.
8. The system of any one of clauses 1 to 7, wherein the graphical user interface comprises an internet website menu interface.
9. The system of any one of clauses 1 to 8, wherein the input manager is configured to receive a plurality of labelled biomolecule requests.
10. The system of clause 9, wherein the input manager is configured to simultaneously receive a plurality of biomolecule requests and label requests.
11. The system of clause 9, wherein the input manager is configured to receive a plurality of biomolecule requests and label requests from the same user.
12. The system of clause 9, wherein the input manager is configured to receive a plurality of biomolecule requests and label requests from a plurality of users.
13. The system of any one of clauses 1 to 12, wherein the memory comprises algorithm for providing a recommendation for an alternative biomolecule when a biomolecule storage identifier that corresponds to the biomolecule request is not available.
14. The system of any one of clauses 1 to 13, wherein the memory comprises algorithm for providing a recommendation for an alternative label when a label storage identifier that corresponds to the label request is not available.
15. The system of any one of clauses 1 to 14, further comprising a reagent preparatory apparatus for preparing the labelled biomolecule reagent, wherein the reagent preparatory apparatus is operatively coupled to the output manager and is configured to:
   receive the identified biomolecule storage identifier and label storage identifier; and
   produce a labelled biomolecule reagent corresponding to the received biomolecule storage identifier and the label storage identifier.
16. The system of clause 15, wherein the reagent preparatory apparatus comprises a sampling device configured to provide an activated biomolecule and an activated label to a contacting apparatus.
17. The system of clause 16, further comprising a contacting apparatus configured for contacting the activated biomolecule with the activated label to produce the labelled biomolecule reagent.
18. The system of any one of clauses 16 to 17, further comprising a labelled biomolecule reagent analyzer.
19. The system of clause 18, wherein the analyzer comprises a purification component for purifying the labelled biomolecule reagent.
20. The system of clause 19, wherein the purification component comprises liquid chromatography.
21. The system of any one of clauses 16 to 20, further comprising a solvent chamber configured to provide one or more solvents to the contacting apparatus.
22. The system of any one of clauses 16 to 21, wherein the contacting apparatus is a microtube.
23. The system of any one of clauses 15 to 22, wherein the system comprises a reagent packaging unit configured to seal the produced labelled biomolecule reagent in the container.
24. The system of any one of clauses 1 to 23, wherein the biomolecule is a compound selected from the group consisting of a polypeptide, a nucleic acid and a polysaccharide.
25. The system of clause 24, wherein the nucleic acid is an oligonucleotide, DNA or RNA.
26. The system of clause 25, wherein the biomolecule is an oligonucleotide.
27. The system of clause 24, wherein the polypeptide is a protein, enzyme or antibody.
28. The system of clause 27, wherein the biomolecule is an antibody.

29. The system of any one of clauses 1 to 28, wherein the label is a compound selected from the group consisting of a fluorophore, chromophore, enzyme, redox label, radiolabels, acoustic label, Raman (SERS) tag, mass tag, isotope tag, magnetic particle, microparticle and nanoparticle.

30. The system of any one of clauses 1 to 29, wherein the memory comprises 25 or more biomolecule storage identifiers.

31. The system of clause 30, wherein the memory comprises 25 or more antibody storage identifiers.

32. The system of any one of clauses 1 to 31, wherein the memory comprises 10 or more label storage identifiers.

33. The system of clause 32, wherein the memory comprises 25 or more fluorophore storage identifiers.

34. The system of any one of clauses 1 to 33, wherein activated biomolecule and activated label each independently comprise a covalently coupled reactive linker.

35. A method comprising:
   communicating a request for a labelled biomolecule reagent, the request comprising one or more of:
      a labelled biomolecule request; and
      a biomolecule request and a label request; and
   receiving one or more labelled biomolecule reagents, each labelled biomolecule reagent comprising a biomolecule covalently coupled to a label through a linker.

36. The method of clause 35, further comprising selecting a labelled biomolecule reagent from a first dataset comprising a plurality of labelled biomolecule storage identifiers.

37. The method of any one of clauses 35 to 36, further comprising selecting:
   a biomolecule from a second dataset comprising a plurality of biomolecule storage identifiers; and
   a label from a third dataset comprising a plurality of label storage identifiers.

38. The method of any one of clauses 35 to 37, wherein communicating the request comprises inputting the labelled biomolecule reagent request into a graphical user interface operatively coupled to an input manager of a system configured to receive the labelled biomolecule reagent request.

39. The method of clause 38, wherein the graphical user interface comprises an internet website menu interface.

40. The method of any one of clauses 35 to 39, wherein communicating the labelled biomolecule reagent request comprises providing the labelled biomolecule reagent request by mail, electronic mail or over the telephone.

41. The method of any one of clauses 35 to 40, wherein the method comprises communicating a request for a plurality of labelled biomolecule reagents.

42. The method of clause 41, wherein the request for a plurality of labelled biomolecule reagents comprises a plurality of biomolecule requests and a plurality of label requests.

43. The method of clause 41, wherein the request for a plurality of labelled biomolecule reagents comprises a single biomolecule request and plurality of label requests.

44. The method of clause 41, wherein the request for a plurality of labelled biomolecule reagents comprises a plurality of biomolecule requests and a single label request.

45. The method of any one of clauses 35 to 44, wherein the received labelled biomolecule reagent is sealed in a container.

46. The method of any one of clauses 35 to 44, wherein the biomolecule is a compound selected from the group consisting of a polypeptide, a nucleic acid and a polysaccharide.

47. The method of clause 46, wherein the nucleic acid is an oligonucleotide, DNA or RNA.

48. The method of clause 46, wherein the biomolecule is an oligonucleotide.

49. The method of clause 46, wherein the polypeptide is a protein, an enzyme or an antibody.

50. The method of clause 46, wherein the biomolecule is an antibody.

51. The method of any one of clauses 35 to 50, wherein the label is a compound selected from the group consisting of fluorophore, chromophore, enzyme, redox label, radiolabels, acoustic label, Raman (SERS) tag, mass tag, isotope tag, magnetic particle, microparticle and nanoparticle.

52. The method of clause 51, wherein the label is a fluorophore.

53. A method comprising:
   communicating a request for a labelled biomolecule reagent to a system comprising:
      an input manager that receives a labelled biomolecule reagent request;
      a memory for storing a dataset comprising a plurality of labelled biomolecule storage identifiers;
      a processing module communicatively coupled to the memory and configured to identify one or more labelled biomolecule storage identifiers from the dataset that corresponds to the components of the labelled biomolecule reagent request;
      an output manager for providing the identified labelled biomolecule storage identifiers; and
   receiving a labelled biomolecule reagent comprising a biomolecule covalently coupled to a label.

54. The method of clause 53, wherein the request for a labelled biomolecule reagent comprises a biomolecule request and a label request.

55. The method of any one of clauses 53 to 54, wherein the memory comprises a first dataset comprising a plurality of biomolecule storage identifiers for a plurality of activated biomolecules and a second dataset comprising a plurality of label storage identifiers for a plurality of activated labels.

56. The method of any one of clauses 53 to 55, wherein communicating the request for a labelled biomolecule reagent comprises inputting one or more of: a labelled biomolecule request, a biomolecule request and a label request into a graphical user interface operatively coupled to the input manager.

57. The method of clause 56, wherein the graphical user interface comprises an internet website menu interface.

58. The method of any one of clauses 53 to 57, wherein the method comprises communicating a request for a plurality of labelled biomolecule reagents.

59. The method of clause 58, wherein the request for the plurality of labelled biomolecule reagents comprises a plurality of biomolecule requests and a plurality of label requests.

60. The method of clause 58, wherein the request for the plurality of labelled biomolecule reagents comprises a single biomolecule request and plurality of label requests.

61. The method of clause 58, wherein the request for the plurality of labelled biomolecule reagents comprises a plurality of biomolecule requests and a single label request.

62. The method of any one of clauses 53 to 61, wherein the received labelled biomolecule reagent is sealed in a container.

63. The method of any one of clauses 53 to 62, wherein the biomolecule is a compound selected from the group consisting of a polypeptide, a nucleic acid and a polysaccharide.

64. The method of clause 63, wherein the nucleic acid is an oligonucleotide, DNA or RNA.

65. The method of clause 64, wherein the biomolecule is an oligonucleotide.
66. The method of clause 63, wherein the polypeptide is a protein, an enzyme or an antibody.
67. The method of clause 66, wherein the biomolecule is an antibody.
68. The method of any one of clauses 53 to 67, wherein the label is a compound selected from the group consisting of a fluorophore, chromophore, enzyme, redox label, radiolabels, acoustic label, Raman (SERS) tag, mass tag, isotope tag, magnetic particle, microparticle and nanoparticle.
69. The method of clause 68, wherein the label is a fluorophore.
70. A method comprising:
   receiving a request for a labelled biomolecule reagent, the request comprising one or more of:
      a labelled biomolecule request; and
      a biomolecule request and a label request;
   preparing a labelled biomolecule reagent corresponding to the labelled biomolecule reagent request by contacting an activated biomolecule with an activated label to produce the labelled biomolecule reagent, wherein the preparing comprising selecting an activated biomolecule and an activated label from a storage comprising a plurality of activated biomolecules and a plurality of activated labels.
71. The method of clause 70, wherein the method comprises receiving a request for a plurality of labelled biomolecule reagents.
72. The method of clause 71, wherein the request for a plurality of labelled biomolecule reagents comprises a plurality of biomolecule requests and a plurality of label requests.
73. The method of clause 71, wherein the request for a plurality of labelled biomolecule reagents comprises a single biomolecule request and plurality of label requests.
74. The method of clause 71, wherein the request for a plurality of labelled biomolecule reagents comprises a plurality of biomolecule requests and a single label request.
75. The method of any one of clauses 70 to 74, wherein contacting comprises manually combining the activated biomolecule with the activated label in a contacting apparatus.
76. The method of clause 75, wherein the contacting apparatus is a microtube.
77. The method of any one of clauses 70 to 76, wherein the activated biomolecule and the activated label are contacted in a contacting apparatus of a reagent preparatory apparatus by a computer-controlled sampling device.
78. The method of any one of clauses 70 to 77, further comprising purifying the labelled biomolecule reagent.
79. The method of any one of clauses 70 to 78, further comprising transporting the labelled biomolecule reagent to a remote location.
80. The method of any one of clauses 70 to 79, wherein the request for a labelled biomolecule reagent is received through an internet website.
81. The method of any one of clauses 70 to 80, wherein the request for a labelled biomolecule reagent is received over the telephone.
82. The method of any one of clauses 70 to 81, wherein the request for a labelled biomolecule reagent is received through the mail.
83. The method of any one of clauses 70 to 82, wherein the request for a labelled biomolecule reagent is received through electronic mail.
84. The method of any one of clauses 70 to 83, further comprising providing a recommendation for an alternative labelled biomolecule when the labelled biomolecule corresponding to the request is not available.
85. The method of any one of clauses 70 to 84, further comprising providing a recommendation for an alternative biomolecule when the biomolecule that corresponds to the biomolecule request is not available.
86. The method of any one of clauses 70 to 85, further comprising providing a recommendation for an alternative label when the label that corresponds to the label request is not available.
87. The method of any one of clauses 70 to 86, wherein the biomolecule is a compound selected from the group consisting of a polypeptide, a nucleic acid and a polysaccharide.
88. The method of clause 87, wherein the nucleic acid is an oligonucleotide, DNA or RNA.
89. The method of clause 88, wherein the biomolecule is an oligonucleotide.
90. The method of clause 87, wherein the polypeptide is a protein, an enzyme or an antibody.
91. The method of clause 90, wherein the biomolecule is an antibody.
92. The method of any one of clauses 70 to 91, wherein the label is a compound selected from the group consisting of a fluorophore, chromophore, enzyme, redox label, radiolabels, acoustic label, Raman (SERS) tag, mass tag, isotope tag, magnetic particle, microparticle and nanoparticle.
93. The method of clause 92, wherein the label is a fluorophore.
94. A method comprising:
   receiving a request for a labelled biomolecule reagent with a system comprising:
      an input manager that receives a labelled biomolecule reagent request;
      a memory for storing a dataset comprising a plurality of labelled biomolecule storage identifiers;
      a processing module communicatively coupled to the memory and configured to identify one or more labelled biomolecule storage identifiers from the dataset that corresponds to the components of the labelled biomolecule reagent request;
      an output manager;
   identifying the labelled biomolecule storage identifiers that corresponds with the labelled biomolecule reagent request;
   outputting the identified labelled biomolecule reagent storage identifier.
95. The method of clause 94, wherein the request for a labelled biomolecule reagent comprises a biomolecule request and a label request.
96. The method of any one of clauses 94 to 95, further comprising displaying the outputted labelled biomolecule reagent storage identifier onto an electronic display.
97. The method of any one of clauses 94 to 96, further comprising printing the outputted labelled biomolecule reagent storage identifier.
98. The method of any one of clauses 94 to 97, wherein the method comprises receiving a plurality of requests for labelled biomolecule reagents.
99. The method of clause 98, wherein the plurality of requests are received from the same user.
100. The method of clause 98, wherein the plurality of requests are received from different users.
101. The method of clause 98, wherein the request for the labelled biomolecule reagents comprises a plurality of biomolecule requests and a plurality of label requests.

102. The method of clause 98, wherein the request for the labelled biomolecule reagents comprises a single biomolecule request and plurality of label requests.
103. The method of any one of clauses 94 to 102, wherein the request for the labelled biomolecule reagents comprises a plurality of biomolecule requests and a single label request.
104. The method of clause 103, further comprising contacting an activated biomolecule associated with biomolecule storage identifier with an activated label associated with the label storage identifier to produce the labelled biomolecule reagent.
105. The method of clause 104, wherein contacting comprises manually combining the activated biomolecule with the activated label in a contacting apparatus.
106. The method of clause 105, wherein the contacting apparatus is a microtube.
107. The method of clause 105, wherein the activated biomolecule and the activated label are contacted in a contacting apparatus of a reagent preparatory apparatus by a computer controlled sampling device.
108. The method of clause 105, further comprising purifying the labelled biomolecule reagent.
109. The method of any one of clauses 94 to 108, further comprising transporting the labelled biomolecule reagent to a remote location.
110. The method of any one of clauses 94 to 109, wherein the request for a labelled biomolecule reagent is received through an internet website.
111. The method of any one of clauses 94 to 110, wherein the request for a labelled biomolecule reagent is received over the telephone and inputted into the input manager.
112. The method of any one of clauses 94 to 111, wherein the request for a labelled biomolecule reagent is received through the mail and inputted into the input manager.
113. The method of clause 112, wherein the request fora labelled biomolecule reagent is received through electronic mail and inputted into the input manager.
114. The method of any one of clauses 94 to 113, further comprising providing a recommendation for an alternative labelled biomolecule from a database when a labelled biomolecule storage identifier that corresponds to the labelled biomolecule request is not available.
115. The method of any one of clauses 94 to 114, further comprising providing a recommendation for an alternative biomolecule from a database when a biomolecule storage identifier that corresponds to the biomolecule request is not available.
116. The method of any one of clauses 94 to 115, further comprising providing a recommendation for an alternative label from a database when a label storage identifier that corresponds to the label request is not available.
117. The method of any one of clauses 94 to 116, wherein the biomolecule is a compound selected from the group consisting of a polypeptide, a nucleic acid and a polysaccharide.
118. The method of clause 117, wherein the biomolecule is a nucleic acid.
119. The method of clause 118, wherein the nucleic acid is an oligonucleotide, DNA or RNA.
120. The method of clause 119, wherein the biomolecule is an oligonucleotide.
121. The method of clause 117, wherein the polypeptide is a protein, an enzyme or an antibody.
122. The method of clause 121, wherein the biomolecule is an antibody.
123. The method of any one of clauses 94 to 122, wherein the label is a compound selected from the group consisting of a fluorophore, chromophore, enzyme, redox label, radiolabels, acoustic label, Raman (SERS) tag, mass tag, isotope tag, magnetic particle, microparticle and nanoparticle.
124. The method of clause 123, wherein the label is a fluorophore.
125. A system comprising:
  a plurality of activated biomolecules;
  a plurality of activated labels; and
  a reagent preparatory apparatus for preparing a labelled biomolecule reagent, wherein the reagent preparatory apparatus is configured to:
    receive an identified biomolecule storage identifier and label storage identifier; and
    produce a labelled biomolecule reagent corresponding to the received biomolecule storage identifier and the label storage identifier.
126. The system of clause 125, wherein the reagent preparatory apparatus comprises a sampling device configured to provide an activated biomolecule and an activated label to a contacting apparatus.
127. The system of clause 126, wherein the reagent preparatory apparatus comprises a contacting apparatus configured for contacting the activated biomolecule with the activated label to produce the labelled biomolecule reagent.
128. The system of clause 127, further comprising a labelled biomolecule reagent analyzer.
129. The system of clause 128, wherein the analyzer comprises a purification component for purifying the labelled biomolecule reagent.
130. The system of any one of clauses 125 to 126, wherein the system comprises a reagent packaging unit configured to seal the produced labelled biomolecule reagent in a container.
131. The system of any one of clauses 125 to 130, wherein the reagent preparatory apparatus is operatively coupled to a system for receiving a labelled biomolecule reagent request, the system comprising:
  an input manager for receiving a biomolecule request and a label request for a labelled biomolecule reagent;
  a memory for storing a first dataset comprising a plurality of biomolecule storage identifiers for a plurality of activated biomolecules and a second dataset comprising a plurality of label storage identifiers for a plurality of activated labels;
  a processing module communicatively coupled to the memory and configured to identify a biomolecule storage identifier and a label storage identifier from the first dataset and second dataset that correspond to the biomolecule request and label request;
  an output manager for providing the identified biomolecule storage identifier and label storage identifier.
132. The system of any one of clauses 125 to 131, wherein the system comprises 1000 or more different activated biomolecules.
133. The system of any one of clauses 125 to 132, wherein the biomolecule is selected from the group consisting of a polypeptide, a nucleic acid and a polysaccharide.
134. The system of clause 133, wherein the biomolecule is an oligonucleotide.
135. The system of clause 134, wherein the system comprises 1000 or more different types of oligonucleotides.
136. The system of clause 133, wherein the biomolecule is an antibody.
137. The system of clause 136, wherein the system comprises 1000 or more different types of antibodies.

138. The system of any one of clauses 125 to 137, wherein each activated biomolecule comprises a reactive linker.
139. The system of any one of clauses 125 to 138, wherein the system comprises 100 or more different activated labels.
140. The system of clause 139, wherein the label is selected from the group consisting of a fluorophore, chromophore, enzyme, redox label, radiolabels, acoustic label, Raman (SERS) tag, mass tag, isotope tag, magnetic particle, microparticle and nanoparticle.
141. The system of any one of clauses 125 to 140, wherein activated label comprises a reactive linker.
142. A storage comprising:
  a plurality of activated biomolecules; and
  a plurality of activated labels.
143. The storage of clause 142, wherein the storage comprises 1000 or more different activated biomolecules.
144. The storage of any one of clauses 142 to 143, wherein the biomolecule is selected from the group consisting of a polypeptide, a nucleic acid and a polysaccharide.
145. The storage of clause 144, wherein the biomolecule is an oligonucleotide.
146. The storage of clause 145, wherein the storage comprises 1000 or more different types of oligonucleotides.
147. The storage of clause 144, wherein the biomolecule is an antibody.
148. The storage of clause 147, wherein the storage comprises 1000 or more different types of antibodies.
149. The storage of any one of clauses 142 to 148, wherein each activated biomolecule comprises a reactive linker.
150. The storage of any one of clauses 142 to 149, wherein the storage comprises 100 or more different activated labels.
151. The storage of clause 150, wherein the label of the activated labels is selected from the group consisting of a fluorophore, chromophore, enzyme, redox label, radiolabels, acoustic label, Raman (SERS) tag, mass tag, isotope tag, magnetic particle, microparticle and nanoparticle.
152. A labelled biomolecule reagent dispensing system comprising:
  an input module for receiving a request for a labelled biomolecule;
  a reagent preparatory apparatus; and
  a dispensing module for outputting a packaged labelled biomolecule.
153. The labelled biomolecule reagent dispensing system of clause 152, wherein the input module comprises:
  a graphical user interface for communicating a labelled biomolecule request to an input manager;
  an input manager for receiving a request for a labelled biomolecule;
  a memory for storing a dataset having a plurality of storage identifiers that correspond to the one or more components of the labelled biomolecule reagent request;
  a processing module communicatively coupled to the memory and configured to identify a storage identifier from the dataset that corresponds to the components of the labelled biomolecule reagent request; and
  an output manager for providing the identified storage identifiers.
154. The labelled biomolecule reagent dispensing system of any one of clauses 152 to 153, wherein the reagent preparatory apparatus comprises one or more of a source of a labelled biomolecule, a source of a biomolecule, a source of a label, a source of a reactive linker, a source of an activated biomolecule and a source of an activated label.
155. The labelled biomolecule reagent dispensing system of any one of clauses 152 to 154, wherein the reagent preparatory apparatus comprises:
  a sampling device configured to provide an activated biomolecule and an activated label to a contacting apparatus.
156. The labelled biomolecule reagent dispensing system of clause 155, further comprising a contacting apparatus configured for contacting the activated biomolecule with the activated label to produce the labelled biomolecule reagent.
157. The labelled biomolecule reagent dispensing system of any one of clauses 155 to 156, further comprising a labelled biomolecule reagent analyzer.
158. The labelled biomolecule reagent dispensing system of clause 157, wherein the analyzer comprises a purification component for purifying the labelled biomolecule reagent.
159. The labelled biomolecule reagent dispensing system of clause 158, wherein the purification component comprises liquid chromatography.
160. The labelled biomolecule reagent dispensing system of any one of clauses 153 to 159, further comprising a solvent chamber configured to provide one or more solvents to the contacting apparatus.
161. The labelled biomolecule reagent dispensing system according to any one of clauses 152 to 160, wherein the dispensing module comprises a reagent packaging unit configured to seal the produced labelled biomolecule reagent in the container.
162. The labelled biomolecule reagent dispensing system according to clause 161, wherein the container is selected from the group consisting of a pouch, bag, tube, vial, microtube or bottle.
163. The labelled biomolecule reagent dispensing system according to clause 161, wherein the packaging unit is further configured to dispense the sealed container with labelled biomolecule in a second container.
164. The labelled biomolecule reagent dispensing system according to clause 163, wherein the second container is selected from the group consisting of a pouch, bag, tube, vial, microtube or bottle.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A system for use in preparing a labelled biomolecule reagent, the system comprising:
   an input manager for receiving a request for a labelled biomolecule reagent comprising a label and a biomolecule, wherein the request for a labelled biomolecule reagent comprises a biomolecule request and a label request;
   a memory comprising a first dataset comprising a plurality of biomolecule storage identifiers for a plurality of activated biomolecules and a second dataset comprising a plurality of label storage identifiers for a plurality of activated labels;
   a processing module communicatively coupled to the memory and configured to identify a biomolecule storage identifier from the first dataset corresponding to the biomolecule request and a label storage identifier from the second dataset corresponding to the label request; and
   an output manager for providing the identified storage identifiers.

2. The system of claim 1, wherein the input manager is operatively coupled to a graphical user interface.

3. The system of claim 1, wherein the input manager is configured to receive one or more of:
   a single labelled biomolecule request;
   a plurality of labelled biomolecule requests;
   a single biomolecule request and a single label request;
   a plurality of biomolecule requests and a single label request; and
   a single biomolecule request and a plurality of label requests.

4. The system of claim 3, wherein the input manager is configured to receive a plurality of biomolecule requests and label requests from a plurality of users.

5. The system of claim 1, wherein the memory comprises an algorithm for providing a recommendation for:
   an alternative biomolecule when a biomolecule storage identifier that corresponds to the biomolecule request is not available; or
   an alternative label when a label storage identifier that corresponds to the label request is not available.

6. The system of claim 1, further comprising a reagent preparatory apparatus for preparing the labelled biomolecule reagent, wherein the reagent preparatory apparatus is operatively coupled to the output manager and is configured to:
   receive the identified biomolecule storage identifier and label storage identifier; and
   produce a labelled biomolecule reagent corresponding to the received biomolecule storage identifier and the label storage identifier.

7. The system of claim 1, wherein:
   the biomolecule is a compound selected from the group consisting of a polypeptide, a nucleic acid and a polysaccharide; and
   the label is a compound selected from the group consisting of a fluorophore, a magnetic particle and a nanoparticle.

8. The system of claim 1, wherein the memory comprises:
   25 or more biomolecule storage identifiers; and
   10 or more label storage identifiers.

9. The system of claim 1, wherein the biomolecule and the label are covalently bonded via a reactive linker.

10. A method comprising:
    receiving a request for a labelled biomolecule reagent, the request comprising one or more of:
    a labelled biomolecule request; and
    a biomolecule request and a label request;
    preparing a labelled biomolecule reagent corresponding to the labelled biomolecule reagent request by contacting an activated biomolecule with an activated label to produce the labelled biomolecule reagent, wherein the preparing comprising selecting an activated biomolecule and an activated label from a storage comprising a plurality of activated biomolecules and a plurality of activated labels.

11. A system comprising:
    a plurality of activated biomolecules;
    a plurality of activated labels; and
    a reagent preparatory apparatus for preparing a labelled biomolecule reagent, wherein the reagent preparatory apparatus is configured to:
    receive an identified biomolecule storage identifier and label storage identifier; and
    produce a labelled biomolecule reagent corresponding to the received biomolecule storage identifier and the label storage identifier.

12. The method of claim 10, wherein the method comprises receiving a request for a plurality of labelled biomolecule reagents.

13. The method of claim 12, wherein the request for a plurality of labelled biomolecule reagents comprises a plurality of biomolecule requests and a plurality of label requests.

14. The method of claim 12, wherein the request for a plurality of labelled biomolecule reagents comprises a single biomolecule request and plurality of label requests.

15. The method of claim 12, wherein the request for a plurality of labelled biomolecule reagents comprises a plurality of biomolecule requests and a single label request.

16. The system of claim 11, wherein the reagent preparatory apparatus comprises a sampling device configured to provide an activated biomolecule and an activated label to a contacting apparatus.

17. The system of claim 16, wherein the reagent preparatory apparatus comprises a contacting apparatus configured for contacting the activated biomolecule with the activated label to produce the labelled biomolecule reagent.

18. The system of claim 17, further comprising a labelled biomolecule reagent analyzer.

* * * * *